United States Patent
Yoo et al.

(10) Patent No.: US 9,782,767 B2
(45) Date of Patent: Oct. 10, 2017

(54) SULFONATE-BASED COMPOUND AND POLYMER ELECTROLYTE MEMBRANE USING SAME

(71) Applicant: LG CHEM, LTD., Seoul (KR)

(72) Inventors: Joungeun Yoo, Daejeon (KR); Chong Kyu Shin, Daejeon (KR); Seungpyo Jeong, Daejeon (KR); Youngjea Kim, Daejeon (KR); Jong-Chan Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 175 days.

(21) Appl. No.: 14/652,741

(22) PCT Filed: Jun. 12, 2014

(86) PCT No.: PCT/KR2014/005172
§ 371 (c)(1),
(2) Date: Jun. 16, 2015

(87) PCT Pub. No.: WO2014/200286
PCT Pub. Date: Dec. 18, 2014

(65) Prior Publication Data
US 2015/0328630 A1 Nov. 19, 2015

(30) Foreign Application Priority Data
Jun. 14, 2013 (KR) ........................ 10-2013-0068547

(51) Int. Cl.
| | | |
|---|---|---|
| *H01M 8/10* | (2016.01) | |
| *B01J 39/18* | (2017.01) | |
| *C07C 309/10* | (2006.01) | |
| *C07F 1/06* | (2006.01) | |
| *C08J 5/22* | (2006.01) | |
| *H01M 8/1004* | (2016.01) | |
| *H01M 8/1048* | (2016.01) | |
| *H01M 8/1018* | (2016.01) | |

(52) U.S. Cl.
CPC .......... *B01J 39/185* (2013.01); *C07C 309/10* (2013.01); *C07F 1/06* (2013.01); *C08J 5/2262* (2013.01); *H01M 8/1004* (2013.01); *H01M 8/1048* (2013.01); *C08J 2371/00* (2013.01); *C08J 2371/12* (2013.01); *H01M 2008/1095* (2013.01)

(58) Field of Classification Search
CPC ........ B01J 39/185; C07C 309/10; C07F 1/06; C08G 75/23; C08J 5/2262; C08J 2371/00; C08J 2371/12; H01M 8/1004; H01M 8/1048; H01M 2008/1095
See application file for complete search history.

(56) References Cited

U.S. PATENT DOCUMENTS

| | | | | |
|---|---|---|---|---|
| 2,573,769 | A | | 11/1951 | Lambrech |
| 7,473,714 | B2 * | | 1/2009 | Einsla ................ C08G 65/48 429/303 |
| 7,807,759 | B2 * | | 10/2010 | Shin ................... C08G 65/4056 429/492 |
| 8,222,367 | B2 | | 7/2012 | Lalgudi et al. |
| 9,136,551 | B2 | | 9/2015 | Kwon et al. |
| 2002/0192530 | A1 * | | 12/2002 | Kabumoto .......... H01M 8/0234 429/450 |
| 2004/0219413 | A1 * | | 11/2004 | Kim ...................... H01B 1/122 429/494 |
| 2006/0134494 | A1 * | | 6/2006 | Shin ................... C08G 65/4056 429/494 |
| 2007/0292730 | A1 * | | 12/2007 | McGrath ............ C08G 65/4056 429/494 |
| 2008/0004443 | A1 * | | 1/2008 | Brunelle ............. C08G 65/4012 544/162 |
| 2009/0163692 | A1 * | | 6/2009 | Moore ................. C07C 317/14 528/174 |
| 2009/0221787 | A1 * | | 9/2009 | Haring .................. B01D 71/52 528/391 |
| 2009/0278083 | A1 * | | 11/2009 | Fuller .................... C08J 5/2275 252/182.1 |
| 2010/0297519 | A1 * | | 11/2010 | Kim ..................... H01M 4/8605 429/452 |
| 2014/0065512 | A1 | | 3/2014 | Kwon et al. |

FOREIGN PATENT DOCUMENTS

| | | | |
|---|---|---|---|
| FR | 1300758 | A | 8/1962 |
| GB | 1000662 | A | 8/1965 |
| JP | 2007149653 | A * | 6/2007 |
| KR | 10-2013-0062252 | A | 6/2013 |
| WO | 2013081437 | A1 | 6/2013 |

OTHER PUBLICATIONS

Xu et al., "Highly Conductive Aromatic Ionomers with Perfluorosulfonic Acid Side Chains for Elevated Temperature Fuel Cells," Macromolecules 44: 4605-4609 (2011).

Paillard, E. et al. Polymer electrolytes based on new aryl-containing lithium perfluorosulfonates. Journal of Fluorine Chemistry. Feb. 2012.

Dimitrov et al., "Synthesis and ATRP of novel fluorinated aromatic monomer with pendant sulfonate group," Journal of Fluorine Chemistry 149: 30-35 (2013).

* cited by examiner

*Primary Examiner* — Gregg Cantelmo
(74) *Attorney, Agent, or Firm* — Dentons US LLP

(57) ABSTRACT

The present specification relates to a sulfonate-based compound and a polymer electrolyte membrane using the same, a membrane electrode assembly including the same, and a fuel cell including the same.

16 Claims, 2 Drawing Sheets

[FIGURE 1]
PRIOR ART
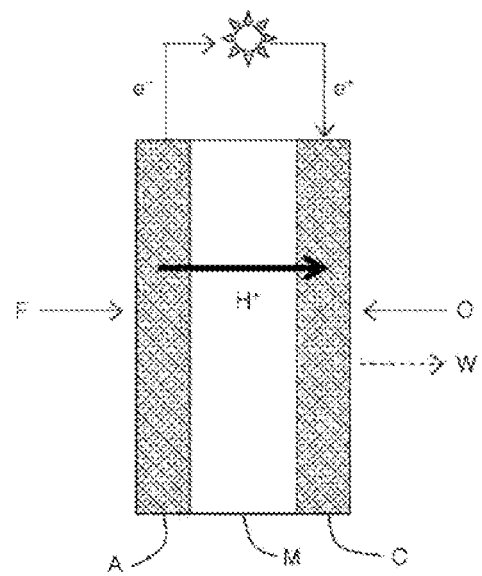
[FIGURE 2]
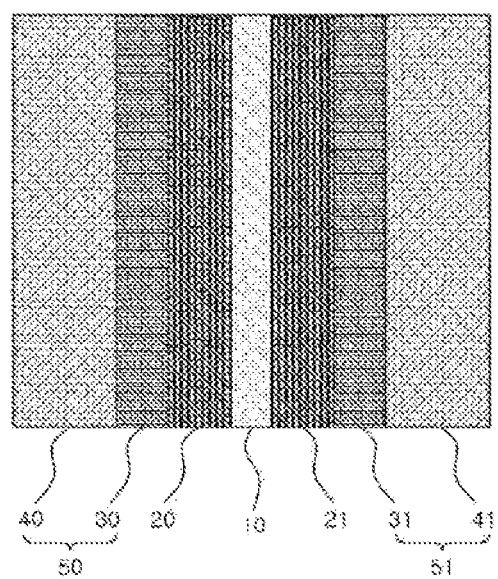

[Figure 3]
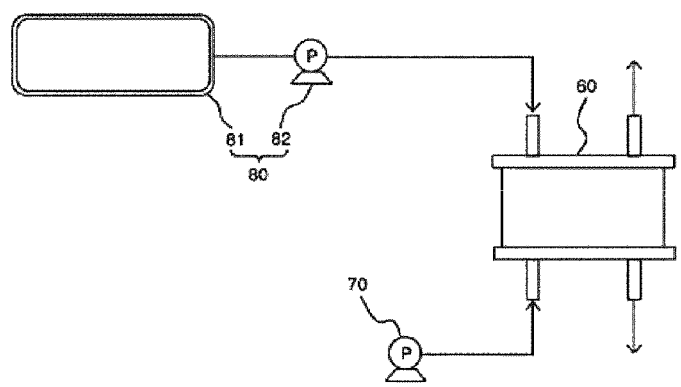

SULFONATE-BASED COMPOUND AND POLYMER ELECTROLYTE MEMBRANE USING SAME

This application is a National Stage Application of International Application No. PCT/KR2014/005172, filed Jun. 12, 2014, and claims the benefit of Korean Application No. 10-2013-0068547, filed Jun. 14, 2013, all of which are hereby incorporated by reference in their entirety for all purposes as if fully set forth herein.

TECHNICAL FIELD

The present specification relates to a sulfonate-based compound and a polymer electrolyte membrane using the same.

BACKGROUND ART

A solid polymer-type fuel cell (hereinafter referred to as a "fuel cell" in some cases) is a power-generating device that generates electricity using the chemical reaction of a fuel gas (examples thereof include hydrogen) with oxygen, and is greatly expected to play a role as one of the next-generation resources for energy in the fields of electric appliance industry, automobile industry, or the like. The fuel cell is composed of a basic unit having two catalyst layers and a polymer electrolyte membrane interposed between the two catalyst layers.

When the power-generating mechanism of a fuel cell using hydrogen as a fuel gas as a typical fuel cell is briefly described, hydrogen is ionized on one catalyst layer to produce hydrogen ions, and the produced hydrogen ions are conducted (ion conduction) to the other catalyst layer through the polymer electrolyte membrane, in which the hydrogen ions are reacted with oxygen to form water. In this case, when the two catalyst layers are connected to an external circuit, an electric current flows to supply electric power to the external circuit. The ionic conduction of the polymer electrolyte membrane is exhibited by the movement of ions along with the movement of water through hydrophilic channels in the polymer electrolyte membrane, and thus, it has been required to maintain the polymer electrolyte membrane in the wet state in order to exhibit ionic conduction efficiently. Such a power-generating mechanism makes the wet state of the polymer electrolyte membrane constituting the fuel cell changed according to the starting and stopping of the fuel cells. When the wet state of the polymer electrolyte membrane is changed as described above, the polymer electrolyte membrane is subjected to alternating between swelling and shrinkage by water absorption/drying, and thus, a defect sometimes occurs in that the interface between the polymer electrolyte membrane and the catalyst layer is microscopically damaged. Further, in extreme cases, failure of the fuel cell may also be caused.

Therefore, the polymer electrolyte membrane used in fuel cells is required to be capable of exhibiting ionic conductivity efficiently at a low water absorption ratio enough to further reduce the swelling and shrinkage (dimensional change from water absorption) according to water absorption and drying.

DETAILED DESCRIPTION OF THE INVENTION

Technical Problem

The present specification has been made in an effort to provide a sulfonate-based compound and a polymer electrolyte membrane using the same.

Technical Solution

The present specification provides a sulfonate-based compound represented by the following Formula 1.

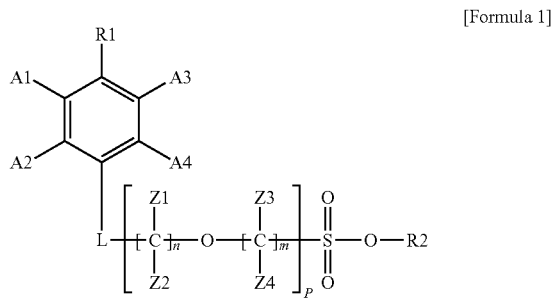

[Formula 1]

In Formula 1,

A1 to A4 are the same as or different from each other, and are each independently a halogen group, R1 is hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, L is a linking group including one or more of O, S, and $SO_2$, Z1 to Z4 are each independently the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, R2 is one of the elements of Group 1 of the periodic table, n is an integer of 0 or more, m is an integer of 0 or more, p is an integer of 1 or more, and {(n×p)+(m×p)} is an integer of 1 to 20.

The present specification provides a polymer electrolyte membrane including the sulfonate-based compound.

Further, the present specification provides a polymer electrolyte membrane which includes a polymer including a monomer derived from the sulfonate-based compound.

In addition, the present specification provides a membrane-electrode assembly including: an anode; a cathode which is provided to face the anode; and an electrolyte membrane which is provided between the anode and the cathode, in which the electrolyte membrane is the polymer electrolyte membrane.

Furthermore, the present specification provides a polymer electrolyte-type fuel cell including: a stack which includes two or more membrane-electrode assemblies and a bipolar plate interposed between the membrane-electrode assemblies; a fuel supply unit which supplies fuel to the stack; and an oxidant supply unit which supplies an oxidant to the stack.

Advantageous Effects

A polymer electrolyte membrane prepared by using the sulfonate-based compound of the present specification easily forms a hydrophilic-hydrophobic phase separation structure.

Further, a polymer electrolyte membrane including the sulfonate-based compound of the present specification efficiently forms a hydrophilic channel in the polymer electrolyte membrane by controlling a phase separation structure.

In addition, a polymer electrolyte membrane including the sulfonate-based compound of the present specification is excellent in ionic conductivity.

Furthermore, a polymer electrolyte membrane including the sulfonate-based compound of the present specification has a low ion exchange capacity (IEC) value.

Further, a fuel cell including the polymer electrolyte membrane is excellent in durability and efficiency.

BRIEF DESCRIPTION OF DRAWINGS

FIG. 1 is a schematic view illustrating an electricity-generating principle of a fuel cell.

FIG. 2 is a view schematically illustrating a structure of a membrane electrode assembly for a fuel cell.

FIG. 3 is a view schematically illustrating an exemplary embodiment of the fuel cell.

EXPLANATION OF REFERENCE NUMERALS AND SYMBOLS

10: Electrolyte membrane
20, 21: Catalyst layer
30, 31: Microporous layer
40, 41: Electrode substrate
50, 51: Gas diffusion layer
60: Stack
70: Oxidant supply unit
80: Fuel supply unit
81: Fuel tank
82: Pump

BEST MODE

Hereinafter, the present specification will be described in more detail.

The present specification provides the sulfonate-based compound represented by Formula 1.

According to an exemplary embodiment of the present invention, L of Formula 1 may be S, O, or $SO_2$.

According to an exemplary embodiment of the present application, R1 may be hydrogen.

According to an exemplary embodiment of the present specification, R2 may be H, Na, or K.

According to an exemplary embodiment of the present specification, R2 may be linked to adjacent hydrogen through an ionic bond.

According to an exemplary embodiment of the present specification, L may be a linking group of —O—, —S—, or —$SO_2$—.

According to an exemplary embodiment of the present specification, Z1 to Z4 of Formula 1 may be each independently selected from the group consisting of F, Cl, Br, and I.

In the case where the sulfonate-based compound of the present specification is included in a polymer electrolyte membrane, when Z1 to Z4 of the sulfonate-based compound are each independently a halogen element (F, Cl, Br, and I), there is an advantage in that the sulfonate-based compound of the present specification may attract electrons well to facilitate the movement of electron ions, and may strengthen the structure of the polymer electrolyte membrane. Specifically, according to an exemplary embodiment of the present specification, the advantage may be maximized when Z1 to Z4 are fluorine.

According to an exemplary embodiment of the present specification, n of Formula 1 may be an integer of 0 to 5.

According to an exemplary embodiment of the present specification, m of Formula 1 may be an integer of 0 to 5.

According to an exemplary embodiment of the present specification, two or more structures in the parenthesis are the same as or different from each other when n of Formula 1 is an integer of 2 or more.

According to an exemplary embodiment of the present specification, two or more structures in the parenthesis are the same as or different from each other when m of Formula 1 is an integer of 2 or more.

According to an exemplary embodiment of the present specification, p of Formula 1 may be an integer of 1 to 5.

According to another exemplary embodiment of the present specification, two or more structures in the parenthesis are the same as or different from each other when p of Formula 1 is an integer of 2 or more.

According to an exemplary embodiment of the present specification, a chain composed of carbon and oxygen of Formula 1 may serve to facilitate a phase separation phenomenon of the polymer electrolyte membrane.

In addition, according to an exemplary embodiment of the present specification, a chain composed of carbon and oxygen of Formula 1 may serve to facilitate the movement of hydrogen ions of the polymer electrolyte membrane.

According to an exemplary embodiment of the present specification, when $\{(n \times p)+(m \times p)\}$ of the chain composed of carbon and oxygen of Formula 1 exceeds 20, a problem in that hydrophilic blocks are excessively formed in the polymer electrolyte membrane may be caused. Therefore, when $\{(n \times p)+(m \times p)\}$ of Formula 1 is 1 to 20, an appropriate phase separation phenomenon may be caused to enhance the performance of the polymer electrolyte membrane.

Furthermore, according to an exemplary embodiment of the present specification, $\{(n \times p)+(m \times p)\}$ of Formula 1 may be an integer of 3 to 10.

According to an exemplary embodiment of the present specification, A1 is fluorine.

According to another exemplary embodiment, A2 is fluorine.

According to an exemplary embodiment of the present specification, A3 is fluorine.

According to another exemplary embodiment, A4 is fluorine.

According to an exemplary embodiment of the present specification, the sulfonate-based compound represented by Formula 1 may be a compound represented by any one of the following Formulae 2-1 to 2-3.

[Formula 2-1]

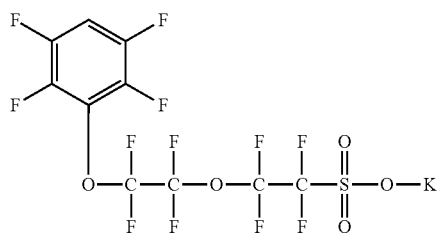

[Formula 2-2]

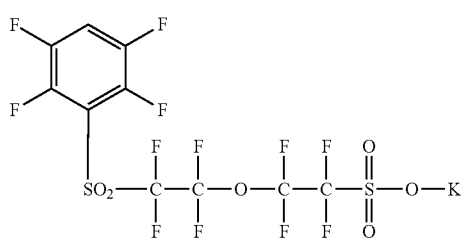

[Formula 2-3]

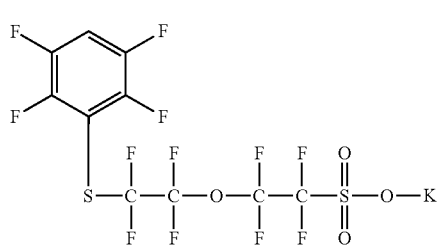

The present specification provides a polymer electrolyte membrane including the sulfonate-based compound. Specifically, the sulfonate-based compound may be included in the polymer electrolyte membrane as a monomer, or as an additive.

Since the existing fluorine-based electrolyte membrane among electrolyte membranes for a fuel cell is expensive, development of a relatively inexpensive hydrocarbon-based electrolyte membrane has been attempted. Since the phase separation of hydrophilicity and hydrophobicity is important in the electrolyte membrane, a block polymer may be used, but when the distance between the main chain and a sulfone group is short in the hydrocarbon-based block polymer, it is difficult to obtain the phase separation. However, since there is a halogen group between a phenyl group, which is an aromatic group, and a sulfone group, specifically, a linking group including fluorine, particularly, an aliphatic group including fluorine, the sulfonate-based compound may provide an electrolyte membrane having an enhanced phase separation property.

According to an exemplary embodiment of the present specification, the polymer electrolyte membrane may include a polymer including a monomer derived from the sulfonate-based compound.

When the sulfonate-based compound is a monomer polymerized in a polymer, the polymer including the sulfonate-based compound may a homopolymer of the sulfonate-based compound, and may also include an additional co-monomer. As the additional co-monomer, those known in the art may be used. In this case, one or two or more of the co-monomer may be used.

Examples of the co-monomer include a monomer constituting a perfluorosulfonic acid polymer, a hydrocarbon-based polymer, polyimide, polyvinylidene fluoride, polyethersulfone, polyphenylene sulfide, polyphenylene oxide, polyphosphazine, polyethylene naphthalate, polyester, doped polybenzimidazole, polyether ketone, polysulfone, and acids or bases thereof.

The polymer may further include other sulfonate-based compounds in addition to the sulfonate-based compound.

As a specific example, the polymer may be a polymer in which 4,4'-difluorobenzophenone and 3,5-bis(4-fluorobenzoyl)phenyl(4-fluorophenyl)methanone are polymerized with the sulfonate-based compound. Herein, a sulfonate-based compound such as a hydroquinone sulfonic acid potassium salt may be additionally included.

As another example, the polymer may be a multi-block copolymer obtained by further adding 4,4'-difluorobenzophenone, 9,9-bis(hydroxyphenyl)fluorine, and 3,5-bis(4-fluorobenzoyl)phenyl(4-fluorophenyl)-methanone to a polymer in which 4,4'-difluorobenzophenone and 3,5-bis(4-fluorobenzoyl)phenyl(4-fluorophenyl)methanone are polymerized with the sulfonate-based compound, and reacting the mixture.

When an additional co-monomer is used in the polymer in addition to the sulfonate-based compound, the content of the additional co-monomer in the polymer may be, for example, more than 0% by weight and 95% by weight or less.

The content of the sulfonate-based compound and the additional co-monomer in the polymer may be adjusted depending on an appropriate ion exchange capacity (IEC) value required for an electrolyte membrane for a fuel cell to be applied. In the case of the polymer synthesis for preparation of a separation membrane for a fuel cell, the polymer may be designed by calculating the value of ion exchange capacity (IEC) meq./g=mmol/g. Although the value may vary if necessary, the content of the monomer in the polymer may be selected such that the value is within a range of $0.5 \leq IEC \leq 3$. The sulfonate-based compound may be used to design an electrolyte membrane which has a low IEC value while exhibiting the same ionic conductivity value.

A polymer including the sulfonate-based compound may have a weight average molecular weight of several ten thousands to several million. Specifically, the weight average molecular weight of the polymer may be selected within a range from 100,000 to 1,000,000.

The polymer including the sulfonate-based compound is preferably a block copolymer. The polymer including the sulfonate-based compound may be synthesized by, for example, a condensation polymerization method in which a monomer including a halogen element is used to react F from the monomer and allow HF or HCl to be bonded while being released from the bond.

According to an exemplary embodiment of the present specification, when the sulfonate-based compound is included in a polymer electrolyte membrane, a repeating unit may be formed while fluorine is detached from the 1 and 3 positions of the phenyl group. Specifically, when the sulfonate-based compound represented by Formula 1 is included in a polymer electrolyte membrane, the compound may be included in the polymer electrolyte membrane as a repeating unit represented by the following Formula 1-1.

According to an exemplary embodiment of the present specification, the polymer electrolyte membrane may include a polymer including a monomer derived from a sulfonate-based compound represented by the following Formula 1-1.

[Formula 1-1]

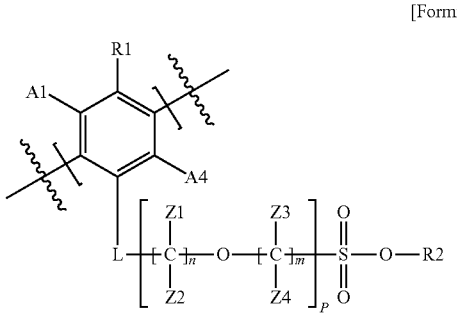

The definition of A1, A4, R1, R2, Z1 to Z4, n, m, and p of the repeating unit represented by Formula 1-1 is the same as that of Formula 1.

According to an exemplary embodiment of the present specification, when the sulfonate-based compound is included in an electrolyte membrane of a polymer as a monomer, fluorine at the 1 and 3 positions of Formulae 2-1 to 2-3 may form a repeating unit while being detached from the sulfonate-based compound.

According to an exemplary embodiment of the present specification, the fluorine substituted at a phenyl group of the repeating unit represented by Formula 1-1 may facilitate the movement of hydrogen ions due to a property of attracting atoms, thereby enhancing the performance of the polymer electrolyte membrane.

When a polymer electrolyte membrane is prepared by using a polymer including the sulfonate-based compound, the polymer electrolyte membrane may be prepared by adding a solvent to the polymer to produce a polymer solution, and then using a solvent casting method to form a film. If necessary, an acid treatment may be performed to convert a $SO_3M$ group into a $SO_3H$ group.

In an exemplary embodiment of the present specification, when the sulfonate-based compound is added to the polymer electrolyte membrane as an additive, the content in the electrolyte membrane is in a range of more than 10% and less than 70%. When the content is 10% or less, the ionic conductivity effect is minimal, and when the content is 70% or more, the sulfonate-based compound is present in an excessive amount to decrease the mechanical strength, and it is difficult to be applied to the membrane. Accordingly, when the sulfonate-based compound is added within the range as an additive, the compound has an ionic conductivity effect and mechanical strength which are appropriate for being applied to the membrane.

When the sulfonate-based compound is included in the polymer electrolyte membrane as an additive, the polymer electrolyte membrane may additionally include one or more polymers of a perfluorosulfonic acid polymer, a hydrocarbon-based polymer, polyimide, polyvinylidene fluoride, polyethersulfone, polyphenylene sulfide, polyphenylene oxide, polyphosphazine, polyethylene naphthalate, polyester, doped polybenzimidazole, polyether ketone, polysulfone, and acids or bases thereof.

Further, in an exemplary embodiment of the present specification, a polymer including a monomer derived from the sulfonate-based compound is included. In an exemplary embodiment of the present specification, the monomer derived from the sulfonate-based compound is included in an amount of 20% by mole to 40% by mole based on the entire polymer. The polymer including a monomer derived from the sulfonate-based compound within the range has high mechanical strength and ionic conductivity.

According to an exemplary embodiment of the present specification, a polymer electrolyte membrane with an appropriate value may be designed depending on the use of a fuel cell to which ionic conductivity and ion exchange capacity of the polymer electrolyte membrane are finally applied, and a material to be added to the polymer electrolyte membrane, for example, the type of monomer or additive to be included in the polymer. For example, when applied to a fuel cell, a polymer electrolyte membrane with $0.5 \leq IEC \leq 3$ and $0.5 \leq IEC \leq 2.5$ may be designed, but the range of the present specification is not limited thereto, and a polymer electrolyte membrane with an appropriate value may be selected if necessary. The polymer electrolyte membrane according to the present specification may have a low IEC value while exhibiting an ionic conductivity value equal to or greater than the ionic conductivity value of the polymer electrolyte membrane in the related art.

According to an exemplary embodiment of the present specification, the ionic conductivity of the polymer electrolyte membrane may be 0.03 s/cm to 0.2 s/cm.

According to an exemplary embodiment of the present specification, the IEC value of the polymer electrolyte membrane may be 0.5 to 3.

When the sulfonate-based compound according to an exemplary embodiment of the present specification is included in the polymer electrolyte membrane as the aforementioned unit, $SO_3R_2$ is linked to each other as a chain in the p parenthesis, and the ionic conductivity of the polymer is high due to easiness in the phase separation between $SO_3R_2$ groups, compared to the case where $SO_3R_2$ is directly bonded to the main chain of the polymer.

The polymer electrolyte membrane according to the present invention may be prepared by using materials or methods in the art, except that the sulfonate-based compound is included.

For example, the polymer electrolyte membrane may be prepared to have a thickness from several micron to several hundreds micron.

According to an exemplary embodiment of the present specification, the polymer electrolyte membrane may be a block-type copolymer including a hydrophilic block and a hydrophobic block.

As used herein, the term "hydrophilic block" refers to a block having an ion exchange group as a functional group. Herein, the functional group may be at least one selected from the group consisting of —$SO_3H$, —$SO_3^-M^+$, —COOH, —COO$^-M^+$, —$PO_3H_2$, —$PO_3H^-M^+$, and —$PO_3^{2-}2M^+$. Herein, M may be a metallic element. That is, the functional group may be hydrophilic.

According to an exemplary embodiment of the present specification, the hydrophilic block may have a weight average molecular weight of 1,000 to 500,000 (g/mol), and the hydrophobic block may have a weight average molecular weight of 1,000 to 500,000 (g/mol).

As used herein, the term "block having an ion exchange group" refers to a block including an average of 0.5 or more expressed as the number of ion exchange groups per one structural unit constituting the corresponding block, and a block having an average of 1.0 or more ion exchange groups per one structural unit is more preferred.

As used herein, the term "hydrophobic block" refers to a polymer block which has substantially no ion exchange group.

As used herein, the term "block having substantially no ion exchange group" refers to a block having an average of less than 0.1 expressed as the number of ion exchange groups per one structural unit constituting the corresponding block, a block having an average of 0.05 or less is more preferred, and a block having no ion exchange group is even more preferred.

Meanwhile, as used herein, the term "block-type copolymer" is a concept that includes copolymers in a copolymerization mode of graft polymerization, in which the block on the one side forms a main chain structure and the block on the other side forms a side chain structure, in addition to those in a copolymerization mode, in which the hydrophilic block and the hydrophobic block form a main chain structure. Meanwhile, the polymer used in the present specification is not limited to the above-described block-type copolymer, and a polymer including a fluorine-based element may also be used. In this case, the polymer including a fluorine-based element may also include a functional group, and the functional group may be hydrophilic. For example, the functional group may be at least one selected from the group consisting of —$SO_3H$, —$SO_3^-M^+$, —COOH, —$COO^-M^+$, —$PO_3H_2$, —$PO_3H^-M^+$, and —$PO_3^{2-}2M^+$. Herein, M may be a metallic element.

O, N, S, Si, and H expressed in the Formulae of the present specification refer to oxygen, nitrogen, sulfur, silicon, and hydrogen, respectively.

According to an exemplary embodiment of the present specification, the repeating unit derived from the sulfonate-based compound may be a repeating unit to be included in the main chain of the hydrophilic block. Specifically, the repeating unit may be included in the form of a repeating unit of Formula 1-1 in the main chain of the hydrophilic block.

According to an exemplary embodiment of the present specification, the polymer electrolyte membrane may be a polymer electrolyte membrane which includes a polymer including a repeating unit represented by the following Formula 3 and a repeating unit represented by the following Formula 4.

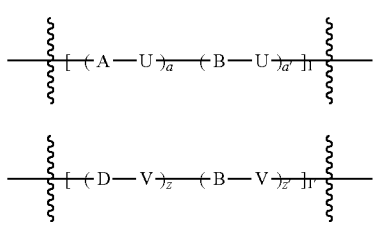

[Formula 3]

[Formula 4]

In Formula 3,
a is an integer more than 0, and
a' is an integer of 0 or more, a:a'=1,000:0 to 5:1, and l is an integer of 1 to 10,000, and
in Formula 4, z is an integer more than 0,
Z' is an integer of 0 or more, z:z'=1,000:0 to 5:1, and l' is an integer of 1 to 100,000, and
in Formulae 3 and 4, A, D, and V are the same as or different from each other, and are each independently represented by one of the following Formulae 3-1 to 3-4,

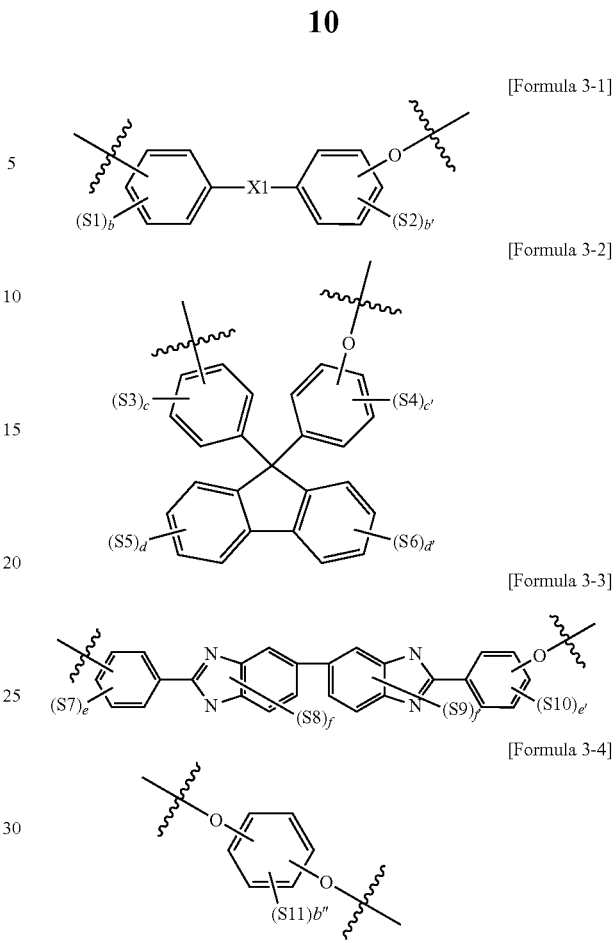

[Formula 3-1]

[Formula 3-2]

[Formula 3-3]

[Formula 3-4]

in Formulae 3-1 to 3-4,
X1 is a direct bond, or one of —C(Z5)(Z6)-, —CO—, —O—, —S—, —$SO_2$—, and —Si(Z5)(Z6)-,
Z5 and Z6 are the same as or different from each other, and are each independently one of hydrogen, an alkyl group, a trifluoromethyl group (—$CF_3$), and a phenyl group,
S1 and S2 are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group,
b and b' are the same as or different from each other, and are each independently an integer of 0 to 4,
S3 to S6 are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, c, c', d and d' are the same as or different from each other, and are each independently an integer of 0 to 4, S7 to S10 are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, e, e', f and f' are the same as or different from each other, and are each independently an integer of 0 to 4, S11 is hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, and b" is an integer of 0 to 4, and in Formula 3, U is represented by one of the following Formulae 4-1 to 4-4 and monomers derived from the sulfonate-based compounds,

[Formula 4-1]

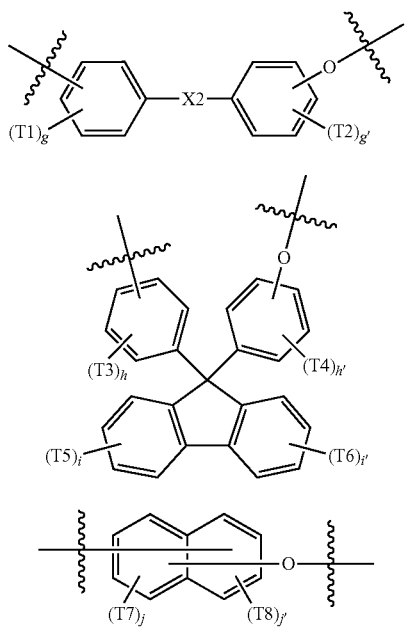

[Formula 4-2]

[Formula 4-3]

[Formula 4-4]

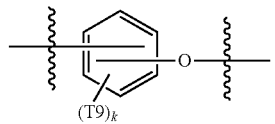

in Formulae 4-1 to 4-4,

X2 is a direct bond, or —CO— or —SO$_2$—, g and g' are the same as or different from each other, and are each independently an integer of 0 to 4, h, h', i and i' are the same as or different from each other, and are each independently an integer of 0 to 4, j and j' are the same as or different from each other, and are each independently an integer of 0 to 3, k's are the same as or different from each other, and are each independently an integer of 0 to 4, T1 to T9 are the same as or different from each other, at least one thereof are each independently —SO$_3$H, —SO$_3^-$M$^+$, —COOH, —COO$^-$M$^+$, —PO$_3$H$_2$, —PO$_3$H$^-$M$^+$, or —PO$_3^{2-}$2M$^+$, M is a metallic element, and the others are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, in Formulas 3 and 4, B is an entirely fluorine-based compound or partially fluorine-based compound, or is represented by any one of the following Formulae 5-1 to 5-3,

[Formula 5-1]

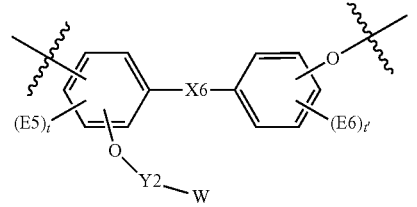

[Formula 5-2]

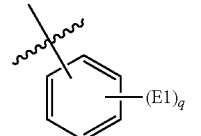

-continued

[Formula 5-3]

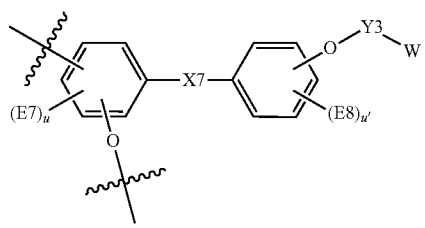

in Formulae 5-1 to 5-3,

X3 to X5 are the same as or different from each other, and are each independently a direct bond, or —CO— or —SO$_2$—, Y1 is a direct bond, or a $C_1$ to $C_{60}$ alkylene group, E1 to E4 are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, and q, r and r' are the same as or different from each other, and are each independently an integer of 0 to 4, s is an integer of 0 to 3, and X6 is a direct bond, or —CO— or —SO$_2$—, Y2 is a direct bond, or a $C_1$ to $C_{60}$ alkylene group, E5 and E6 are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, t is an integer of 0 to 3, t' is an integer of 0 to 4, and X7 is a direct bond, or —CO— or —SO$_2$—, Y3 is a direct bond, or a $C_1$ to $C_{60}$ alkylene group, E7 and E8 are the same as or different from each other, and are each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, u is an integer of 0 to 3, u' is an integer of 0 to 4, and W is represented by the following Formula 6-1 in Formula 3, and represented by the following Formula 6-2 in Formula 4, and

[Formula 6-1]

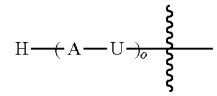

[Formula 6-2]

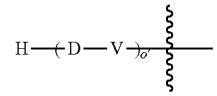

in Formula 6-1, o is an integer of 1 to 10,000, and a definition of A and U is the same as that of A and U in Formula 1, and in Formula 6-2, o' is an integer of 1 to 100,000, and a definition of D and V is the same as that of D and V in Formula 2.

According to an exemplary embodiment of the present specification, Formula 3-1 may be represented by the following Formula 3-1-1.

[Formula 3-1-1]

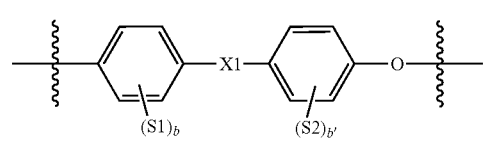

in Formula 3-1-1, X1, S1, S2, b, and b' are the same as those in Formula 3-1.

According to an exemplary embodiment of the present specification, Formula 3-2 may be represented by the following Formula 3-2-1.

[Formula 3-2-1]

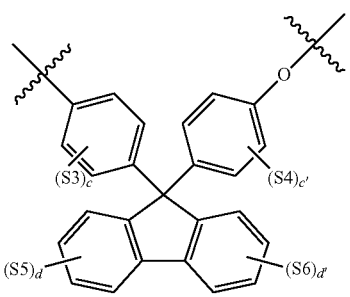

In Formula 3-2-1, S3 to S6, c, c', d, and d' are the same as those in Formula 3-2.

According to an exemplary embodiment of the present specification, Formula 3-3 may be represented by the following Formula 3-3-1.

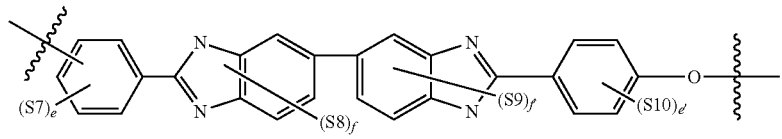
[Formula 3-3-1]
In Formula 3-3-1, S7 to S10, e, e', f, and f' are the same as those in Formula 1-3.
According to an exemplary embodiment of the present specification, A, D, and V of Formulae 3 and 4 are the same as or different from each other, and are at least one selected from the group consisting of
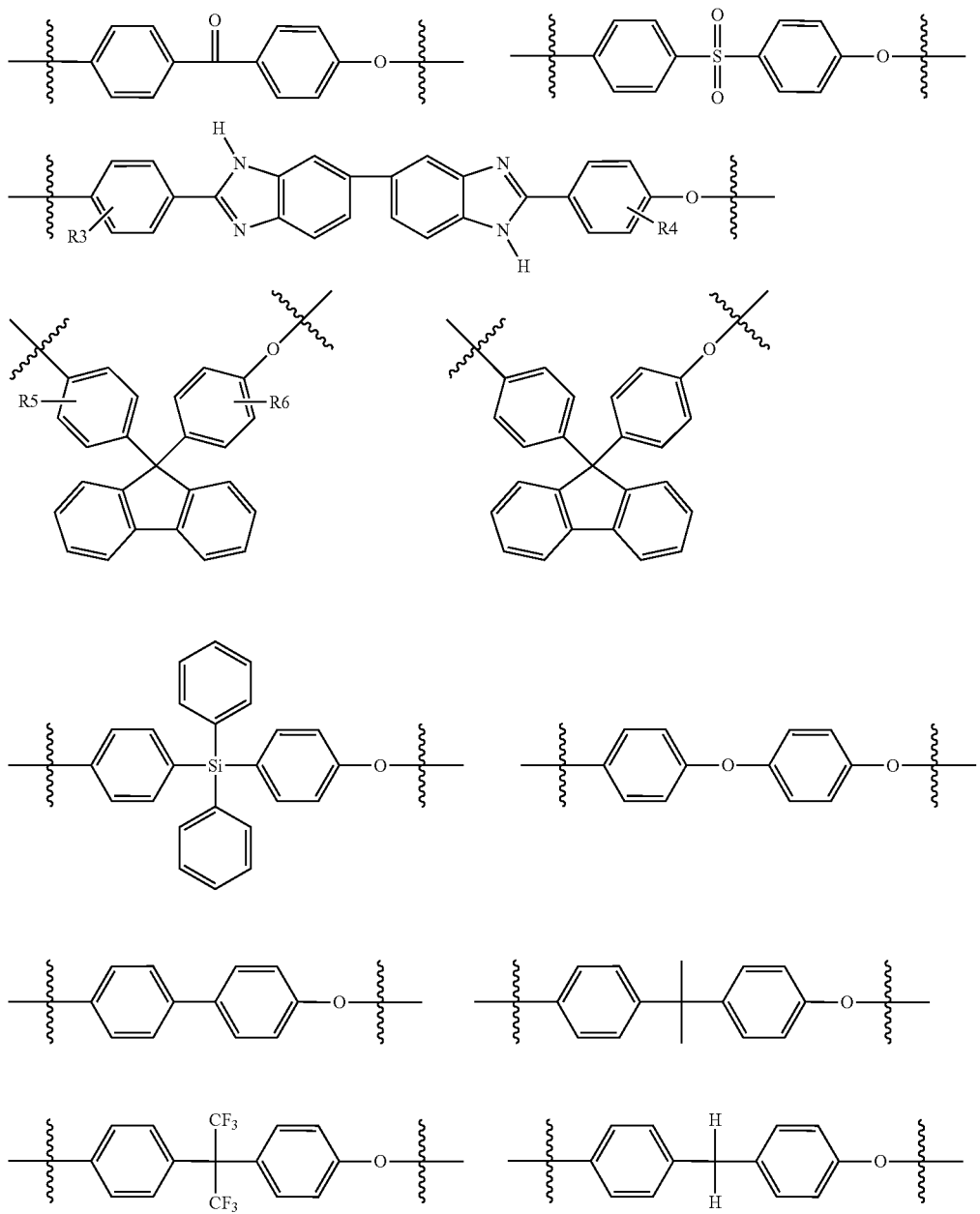

-continued

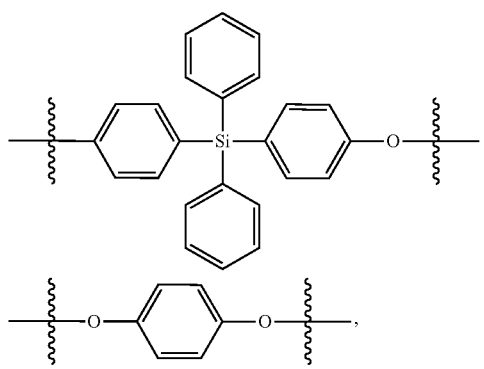
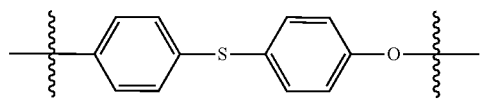

and

R3 to R6 are the same as or different from each other, and may be independently a nitro group (—NO$_2$) or a trifluoromethyl group (—CF$_3$).

According to an exemplary embodiment of the present specification, A, C, and V of Formulae 3 and 4 are the same as or different from each other, and may be

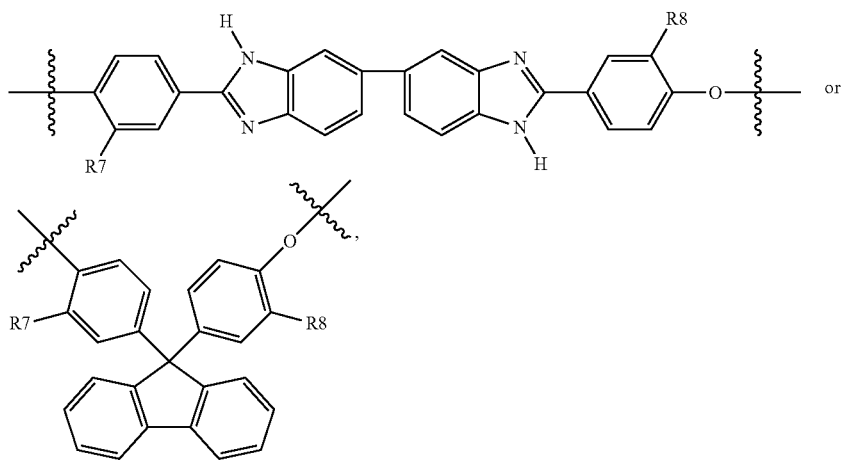

and R7 and R8 are the same as or different from each other, and are independently a nitro group (—NO$_2$) or trifluoromethyl group (—CF$_3$).

According to an exemplary embodiment of the present specification, Formula 4-1 may be represented by the following Formula 4-1-1.

[Formula 4-1-1]

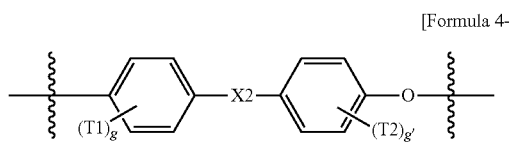

In Formula 4-1-1, X2, T1, T2, g, and g' are the same as those in Formula 4-1.

According to an exemplary embodiment of the present specification, Formula 4-2 may be represented by the following Formula 4-2-1.

[Formula 4-2-1]

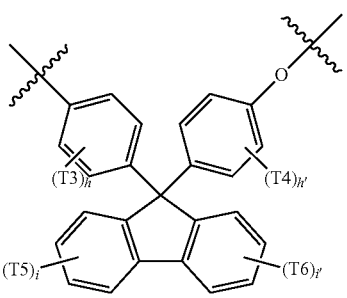

In Formula 4-2-1, T3 to T6, h, h', i, and i' are the same as those in Formula 4-2.

According to an exemplary embodiment of the present specification, Formula 4-3 may be represented by one of the following Formulas 4-3-1 to 4-3-3.

[Formula 4-3-1]

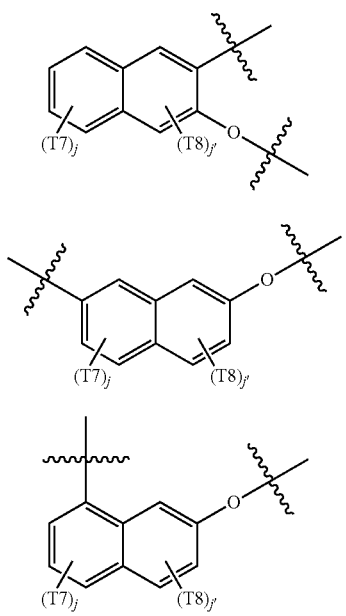

[Formula 4-3-2]

[Formula 4-3-3]

In Formulae 4-3-1 to 4-3-3, T7, T8, j, and j' are the same as those in Formula 4-3.

According to an exemplary embodiment of the present specification, Formula 4-4 may be represented by the following Formula 4-4-1.

[Formula 4-4-1]

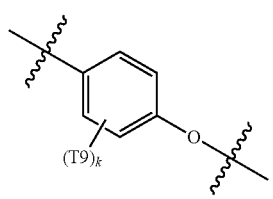

In Formula 4-4-1, T9 and k are the same as those in Formula 4-4.

According to an exemplary embodiment of the present specification, in Formula 3, U is at least one selected from the group consisting of

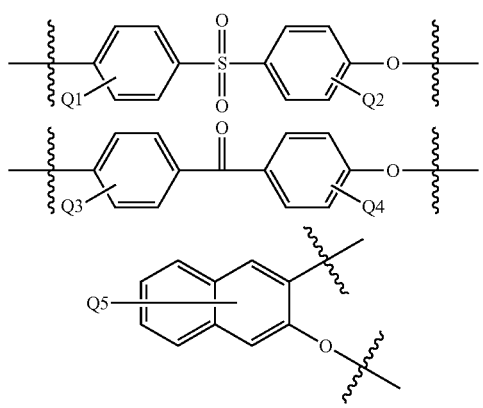

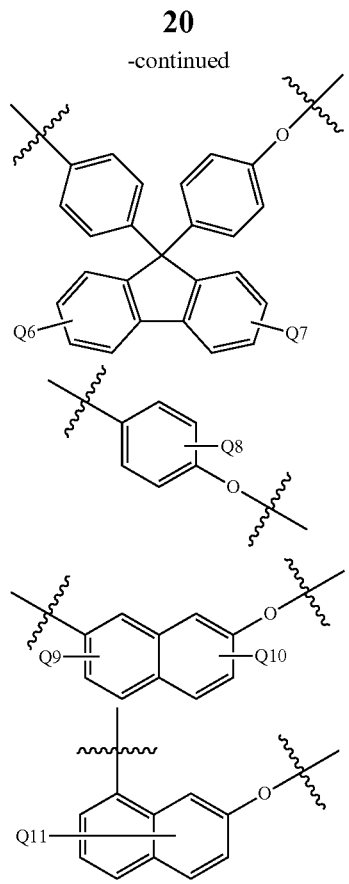

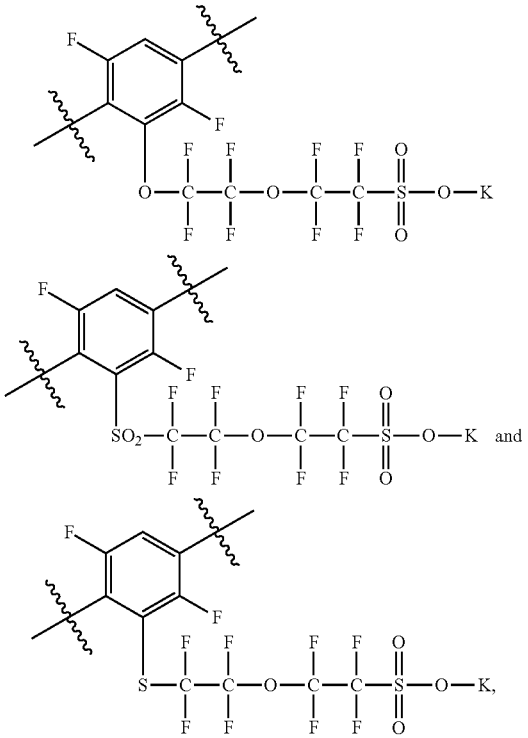

Q1 to Q11 are the same as or different from each other, and are each independently selected from the group consisting of hydrogen, $-SO_3H$, $-SO_3^-M^+$, $-COOH$, $-COO^-M^+$, $-PO_3H_2$, $-PO_3H^-M^+$, and $-PO_3^{2-}2M^+$, and M may be a metallic element.

According to an exemplary embodiment of the present specification, in Formula 3, U is at least one selected from the group consisting of

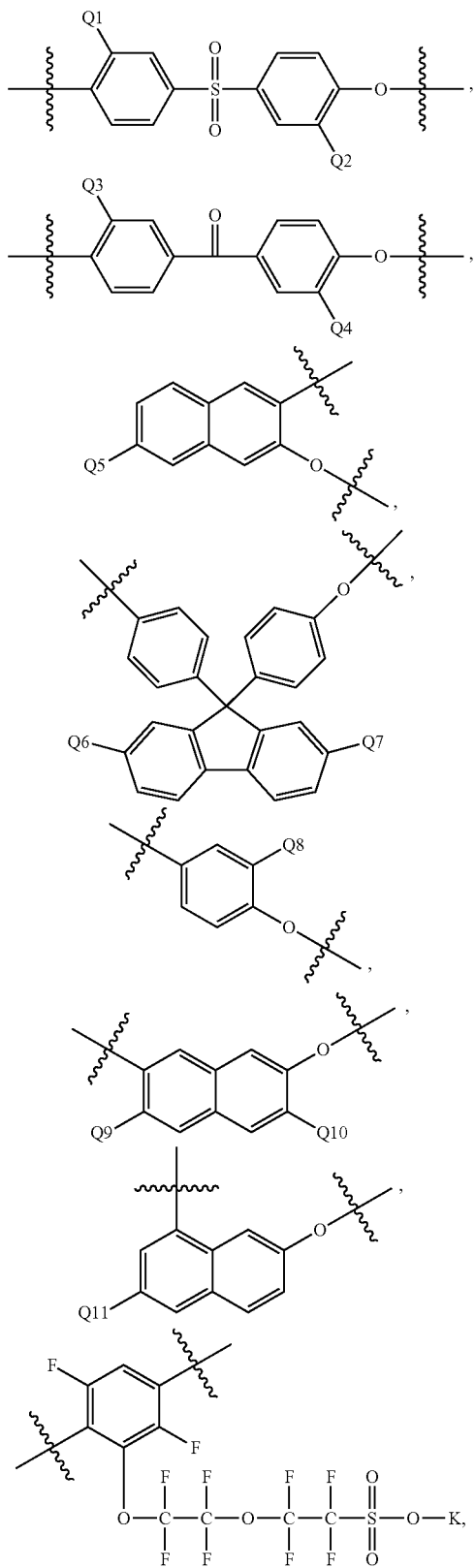

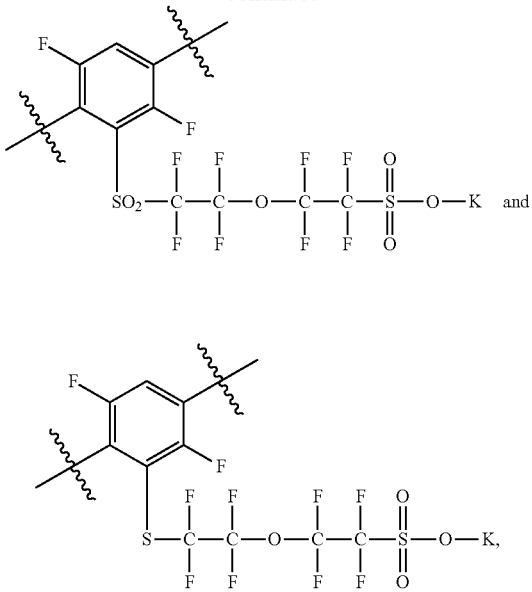

Q1 to Q11 are the same as or different from each other, and are each independently selected from the group consisting of hydrogen, —SO$_3$H, —SO$_3^-$M$^+$, —COOH, —COO$^-$M$^+$, —PO$_3$H$_2$, —PO$_3$H$^-$M$^+$, and —PO$_3^{2-}$2M$^+$, and M may be a metallic element.

According to an exemplary embodiment of the present specification, Formula 5-1 may be represented by the following Formula 5-1-1.

[Formula 5-1-1]

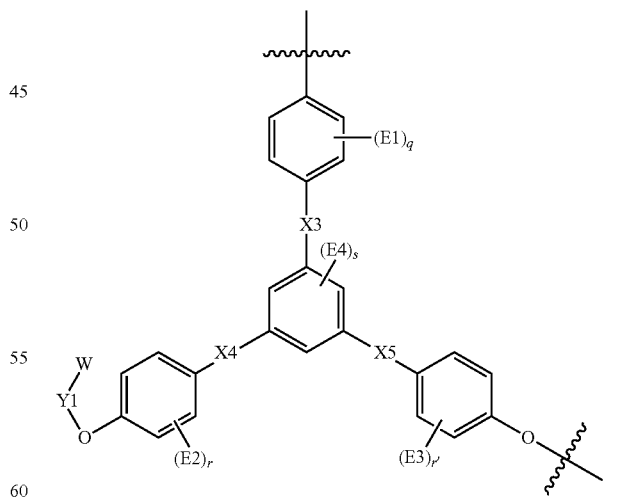

In Formula 5-1-1, X3 to X5, Y1, E1 to E4, W, q, s, r, and r' are the same as those in Formula 5-1.

According to an exemplary embodiment of the present specification, Formula 5-2 may be represented by the following Formula 5-2-2.

[Formula 5-2-2]

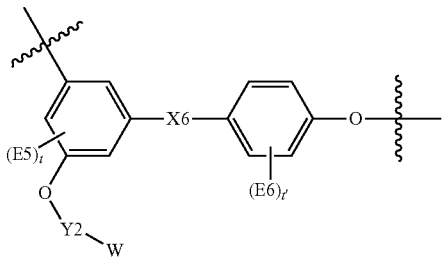

In Formula 5-2-1, X6, Y2, E5, E6, W, t, and t' are the same as those in Formula 5-2.

According to an exemplary embodiment of the present specification, Formula 5-3 may be represented by the following Formula 5-3-1.

[Formula 5-3-1]

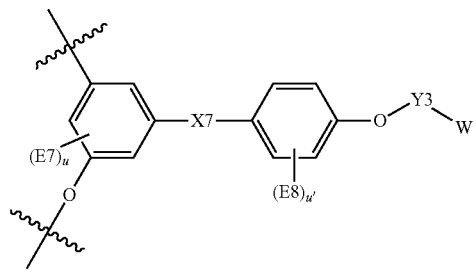

In Formula 5-3-1, X7, Y3, E7, E8, W, u, and u' are the same as those in Formula 5-3.

According to an exemplary embodiment of the present specification, in Formulae 1 and 2, B is one selected from the group consisting of

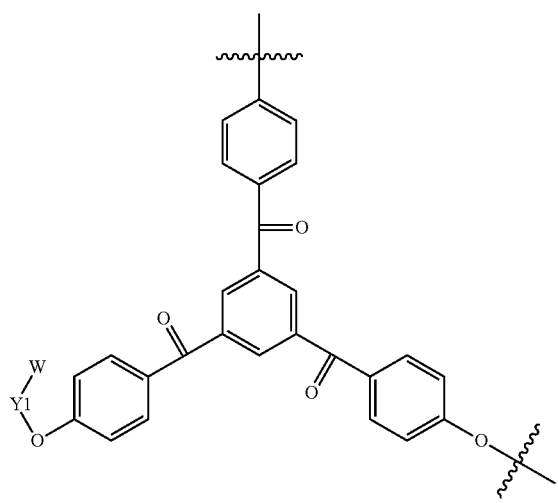

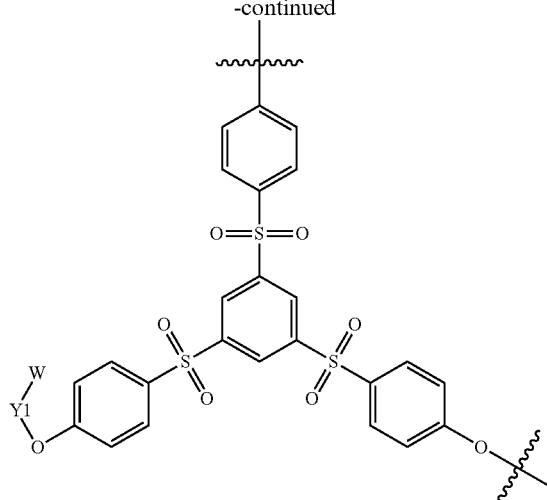

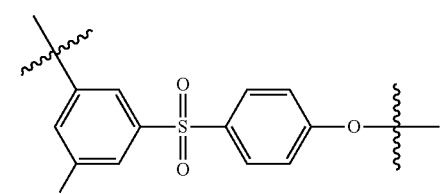

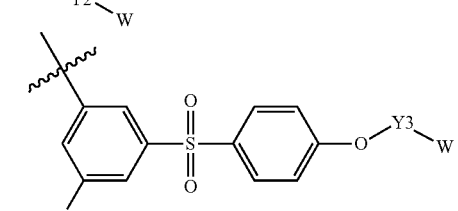

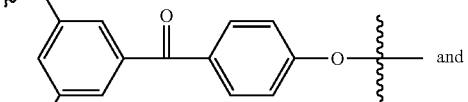

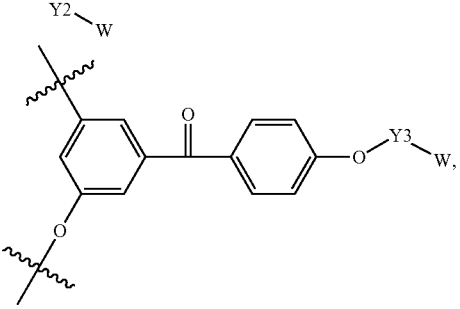

and

Y1 to Y3 are the same as or different from each other, and are each independently a direct bond, or a C1 to C60 alkylene group, and W is a repeating unit represented by the following Formula 6-1 in Formula 3, and a repeating unit represented by the following Formula 6-2 in Formula 4, and

[Formula 6-1]

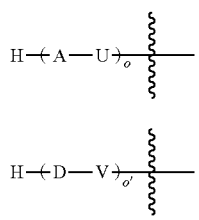

[Formula 6-2]

in Formula 6-1, o is an integer of 1 to 10,000, and a definition of A and U is the same as that of A and U in Formula 3, and in Formula 6-2, o' is an integer of 1 to 100,000, and a definition of D and V may be the same as that of D and V in Formula 4.

According to an exemplary embodiment of the present specification, the block of Formula 3 and the block of Formula 4 in the block-type copolymer polymer may be arranged alternately, in a graft shape, or randomly. m may be a total sum of the numbers of repeating units of Formula 3, which are randomly arranged in the block-type copolymer polymer. n may be a total sum of the numbers of repeating units of Formula 2, which are randomly arranged in the block-type copolymer polymer.

Examples of the substituents of the present specification will be described below, but are not limited thereto.

In the present specification, the aryl group may be monocyclic or polycyclic, and the number of carbon atoms is not particularly limited, but is preferably 6 to 60. Specific examples of the aryl group include a monocyclic aromatic group, such as a phenyl group, a biphenyl group, and a terphenyl group, and a polycyclic aromatic group, such as a naphthyl group, a binaphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and fluoranthene group, but are not limited thereto. In the present specification, the fluorenyl group may be substituted, and adjacent substituents may be combined with each other to form a ring.

When the fluorenyl group is substituted, the fluorenyl group may be

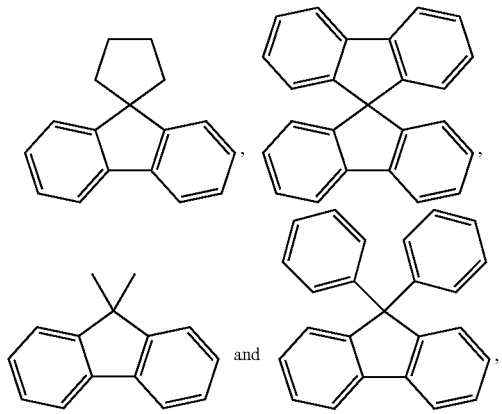

and the like. However, the fluorenyl group is not limited thereto.

In the present specification, the heterocyclic group is a heterocyclic group including one or more of O, N and S atoms as a heteroatom, and the number of carbon atoms is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyrido pyrimidinyl group, a pyrido pyrazinyl group, a pyrazino pyrazinyl group, an isoquinoline group, an indole group, a carbazole group, a benzoxazole group, a benzimidazole group, a benzthiazole group, a benzcarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the alkyl group may be a straight-chain or branched-chain, and the number of carbon atoms is not particularly limited, but is preferably 1 to 50. Specific examples thereof include a methyl group, an ethyl group, a propyl group, an isopropyl group, a butyl group, a t-butyl group, a pentyl group, a hexyl group, a heptyl group and the like, but are not limited thereto.

In the present specification, the alkenyl group may be straight chain or branched chain, and the number of carbon atoms is not particularly limited, but is preferably 2 to 50. Specific examples thereof include preferably an alkenyl group which is substituted with an aryl group such as a stylbenyl group, and a styrenyl group, but are not limited thereto.

In the present specification, the alkoxy group may be a straight chain or branched chain, and the number of carbon atoms is not particularly limited, but is preferably 1 to 50.

In the present specification, the cycloalkyl group is not particularly limited, but has preferably 3 to 60 carbon atoms and is particularly preferably a cyclopentyl group and a cyclohexyl group.

In the present specification, examples of a halogen group include fluorine, chlorine, bromine, or iodine.

In the present specification, the number of carbon atoms of the amine group is not particularly limited, but is preferably 1 to 50. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, the number of carbon atoms of the arylamine group is not particularly limited, but is preferably 6 to 50. Examples of the arylamine group refer to a substituted or unsubstituted monocyclic diarylamine group, a substituted or unsubstituted polycyclic diarylamine group, or a substituted or unsubstituted monocyclic and polycyclic diraylamine group.

Further, as used herein, the term "substituted or unsubstituted" means that a group is substituted with one or more substituents selected from the group consisting of deuterium; a halogen group; an alkyl group; an alkenyl group; an alkoxy group; a cycloalkyl group; a silyl group; an arylalkenyl group; an aryl group; a boron group; an alkylamine group; an aralkylamine group; an arylamine group; an arylamine group; an aryl group; a heterocyclic ring; a nitrile group; a nitro group; a hydroxyl group; and a cyano group, or has no substituent.

As used herein, the term "substitution" means that a hydrogen atom bonded to a carbon atom of a compound is changed into another substituent, and the position to be substituted is not limited as long as the position is a position where the hydrogen atom is substituted, that is, a position where the substituent may be substituted, and when two or more are substituted, the two or more substituents may be the same as or different from each other.

In the present specification,

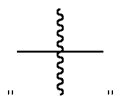

means bonding to an adjacent substituent.

In the present specification, the metallic element may be an alkali metal, an alkaline earth metal, a lanthanide group metal, an actinium group metal, a transition metal, or a post-transition metal.

The alkali metal may be Li, Na, K, Rb, Cs, or Fr.

The alkaline earth metal may be Be, Mg, Ca, Sr, or Ba.

The lanthanide group metal may be La, Ce, Pr, Nd, Pm, Sm, Eu, Gd, Tb, Dy, Ho, Er, Tm, Yb, and Lu.

The actinium group metal may be Ac, Th, Pa, U, Np, Pu, Am, Cm, Bk, Cf, Es, Fm, Md, No, or Lr.

The transition metal may be Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Cn.

The post-transition metal may be Al, Si, P, S, Ga, Ge, As, Se, In, Sn, Sb, Te, Tl, Pb, Bi, or Po.

In the present specification, partially fluorine-based means that fluorine atoms are introduced into only a part of the side chains attached to the main chain of the polymer.

In the present specification, entirely fluorine-based means that fluorine atoms are introduced into all of the side chains of the main chain.

For example, copolymers having a structure of —(—CF$_2$—CF$_2$—)$_n$—, such as PTFE, may be classified to be entirely fluorine-based, and copolymers having a structure of —(—CH$_2$—CF$_2$—)$_n$— such as PVDF, may be classified to be partially fluorine-based. Alternatively, in the case of a copolymer formed of two or more polymers, when one or more polymers among polymers used in the copolymer include a fluorine atom and are used in the copolymer simultaneously with polymers which do not include a fluorine atom, the copolymer may be classified to be partially fluorine-based.

Furthermore, the block-type copolymer may include at least one selected from the group consisting of polystyrene (PS); polyisoprene (PI); polyalkylene; polyalkyleneoxide; polyalkyl(meth)acrylate; poly(2-vinylpyridine) (P2VP); poly(4-vinylpyridine) (P4VP)); poly(meth)acrylic acid (PAA); polyalkyl(meth)acrylic acid; polydialkylsiloxane; polyacrylamide (PAM); poly(ε-caprolactone) (PCL); polylactic acid (PLA); and poly(lactic-co-glycolic acid) (PLGA).

Meanwhile, a membrane-electrode assembly (MEA) may be prepared by using the polymer electrolyte membrane of the present specification. Specifically, the present specification provides a membrane-electrode assembly including: an anode; a cathode which is provided to face the anode; and an electrolyte membrane which is provided between the anode and the cathode, in which the electrolyte membrane is a polymer electrolyte membrane.

The membrane electrode assembly includes a cathode; an anode; and an electrolyte membrane which is disposed between the cathode and the anode, and the electrolyte membrane is the above-described polymer electrolyte membrane according to the present specification.

The membrane electrode assembly (MEA) refers to an assembly of electrodes (cathode and anode) in which an electrochemical catalyst reaction of fuel and air occurs, and a polymer membrane in which the transfer of hydrogen ions occurs, and is a single integration-type unit in which the electrodes (cathode and anode) are adhered to the electrolyte membrane.

The membrane electrode assembly of the present specification is a form to bring a catalyst layer of the anode and a catalyst layer of the cathode into contact with the electrolyte membrane, and may be prepared by a typical method known in the art. As an example, the membrane electrode assembly may be prepared by performing thermocompression at 100° C. to 400° C. while the cathode, the anode, and the electrolyte membrane disposed between the cathode and the anode are closely adhered to each other.

The anode electrode may include an anode catalyst layer and an anode gas diffusion layer. The anode gas diffusion layer may include an anode microporous layer and an anode electrode substrate.

The cathode electrode may include a cathode catalyst layer and a cathode gas diffusion layer. The cathode gas diffusion layer may include an cathode microporous layer and a cathode electrode substrate.

FIG. 1 schematically illustrates the electricity-generating principle of a fuel cell, and the most fundamental unit of generating electricity in the fuel cell is a membrane electrode assembly (MEA), which is composed of an electrolyte membrane (M), and an anode (A) and a cathode (C) electrodes formed on both surfaces of the electrolyte membrane (M). Referring to FIG. 1 which illustrates the electricity-generating principle of the fuel cell, an oxidation reaction of a fuel (F) such as hydrogen or hydrocarbon such as methanol and butane occurs in the anode (A) electrode to generate hydrogen ions (H$^+$) and electrons (e$^-$), and the electron ions move to the cathode (C) electrode through the electrolyte membrane (M). In the cathode (C) electrode, hydrogen ions transferred through the electrolyte membrane (M) are reacted with an oxidant (O) such as oxygen and electrons to produce water (W). The movement of electrons is generated in an external circuit by the reaction.

FIG. 2 schematically illustrates a structure of a membrane electrode assembly for a fuel cell, and the membrane electrode assembly for a fuel cell includes an electrolyte membrane 10, and an anode electrode and a cathode electrode disposed to face each other with the electrolyte membrane 10 interposed therebetween.

The anode electrode is composed of an anode catalyst layer 20 and an anode gas diffusion layer 50, and the anode gas diffusion layer 50 is composed of an anode microporous layer 30 and an anode electrode substrate 40. Herein, the anode gas diffusion layer is provided between the anode catalyst layer and the electrolyte membrane.

The cathode electrode is composed of a cathode catalyst layer 21 and a cathode gas diffusion layer 51, and the cathode gas diffusion layer 51 is composed of a cathode microporous layer 31 and a cathode electrode substrate 41. Herein, the cathode gas diffusion layer is provided between the cathode catalyst layer and the electrolyte membrane.

The catalyst layer of the anode electrode is a place where an oxidation reaction of fuel occurs, and a catalyst selected from the group consisting of platinum, ruthenium, osmium, a platinum-ruthenium alloy, a platinum-osmium alloy, a platinum-palladium alloy, and a platinum-transition metal alloy may be preferably used.

The catalyst layer of the cathode electrode is a place where a reduction reaction of an oxidant occurs, and platinum or a platinum-transition metal alloy may be preferably used as a catalyst. The catalysts may be used as they are, and may be used while being supported in a carbon-based carrier.

The process of introducing a catalyst layer may be performed by a typical method known in the art, and the catalyst layer may be formed by, for example, directly coating a catalyst ink on the electrolyte membrane, or coating a catalyst ink on the gas diffusion layer. In this case, the coating method of the catalyst ink is not particularly limited, but it is possible to use spray coating, tape casting, screen printing, blade coating, die coating or spin coating methods, and the like. The catalyst ink may be representatively composed of a catalyst, a polymer ionomer, and a solvent.

The gas diffusion layer serves as a current conductor and a channel for movement of the reaction gas and water, and has a porous structure. Therefore, the gas diffusion layer may include a conductive substrate. As the conductive substrate, carbon paper, carbon cloth, or carbon felt may be preferably used. The gas diffusion layer may further include a microporous layer between the catalyst layer and the conductive substrate. The microporous layer may be used in order to enhance the performance of a fuel cell under low humid conditions, and serves to maintain the electrolyte membrane in a sufficiently wet state by decreasing the amount of water escaping out of the gas diffusion layer.

Further, the present specification provides a fuel cell including the membrane-electrode assembly (MEA). Specifically, the present specification provides a polymer electrolyte-type fuel cell including: a stack which includes the two or more membrane-electrode assemblies and a bipolar plate interposed between the membrane-electrode assemblies; a fuel supply unit which supplies fuel to the stack; and an oxidant supply unit which supplies an oxidant to the stack.

The fuel cell may be prepared by a typical method known in the art using the membrane electrode assembly (MEA) of the present application. For example, the fuel cell may be prepared to be configured by the membrane electrode assembly (MEA) prepared above and a bipolar plate.

The fuel cell of the present specification includes a stack, a fuel supply unit, and an oxidant supply unit.

FIG. 3 schematically illustrates a structure of a fuel cell, and the fuel cell includes a stack 60, an oxidant supply unit 70, and a fuel supply unit 80.

The stack 60 includes one or two or more of the above-described membrane electrode assemblies, and when two or more membrane electrode assemblies are included, the stack 60 includes a separator interposed between the membrane electrode assemblies. The separator serves to prevent the membrane electrode assemblies from being electrically connected to each other and transfer a fuel and an oxidant externally supplied to the membrane electrode assembly.

The oxidant supply unit 70 serves to provide an oxidant to the stack 60. As the oxidant, oxygen is representatively used, and oxygen or air may be used while being injected with a pump 70.

The fuel supply unit 80 serves to supply fuel to the stack 60, and may be composed of a fuel tank 81 for storing fuel and a pump 82 for supplying the fuel stored in the fuel tank 81 to the stack 60. Hydrogen or a hydrocarbon fuel in the gas or liquid state may be used as the fuel. Examples of the hydrocarbon fuel include methanol, ethanol, propanol, butanol, or natural gas.

A polymer electrolyte fuel cell, a direct liquid fuel cell, a direct methanol fuel cell, a direct formic acid fuel cell, a direct ethanol fuel cell, or a direct dimethyl ether fuel cell, and the like may be used as the fuel cell.

The compound according to the present specification may also be used as a material for various materials, and may be used as a raw material for preparing other materials.

BEST MODE

Hereinafter, the present specification will be described in detail with reference to Examples for specific description. However, the Examples according to the present application may be modified in various forms, and the scope of the present specification is not interpreted as being limited to the Examples to be described below in detail. The Examples of the present specification are provided for more completely explaining the present specification to those skilled in the art.

Example 1

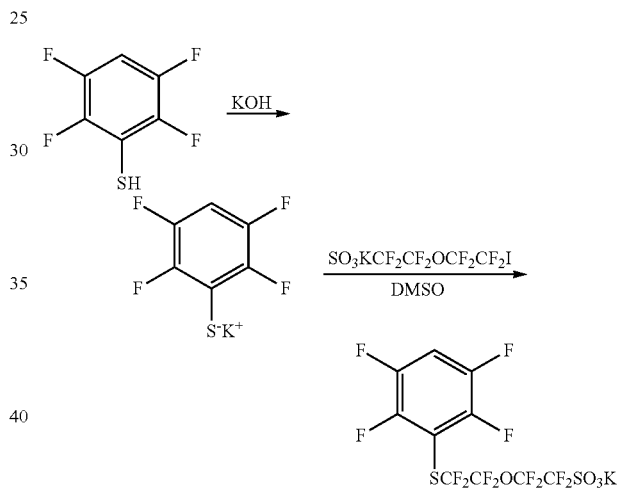

A sulfonate-based compound according to an exemplary embodiment of the present specification was synthesized by using the compound.

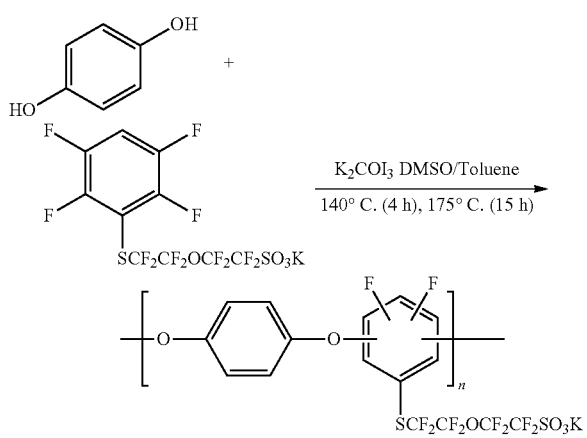

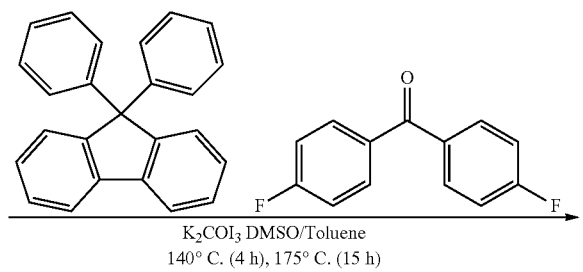

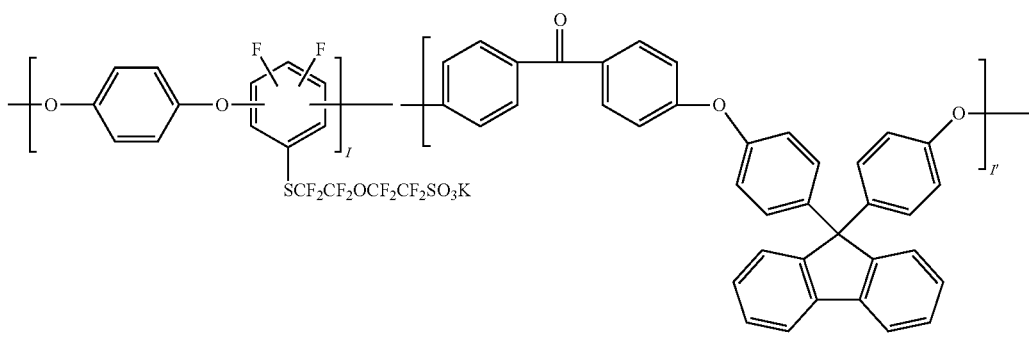

1,4-biphenol (0.001 mol) and the synthesized sulfonate-based compound (0.001 mol) according to an exemplary embodiment of the present specification were polymerized at 140° C. for 4 hours and at 175° C. for 15 hours, and polymerized by using dimethyl sulfoxide (DMSO) as a solvent, and thereafter, the resulting polymer was sufficiently cooled at room temperature, then a secondary monomer (0.0001 mol) was introduced thereto, and toluene and dimethyl sulfoxide (DMSO) were added thereto to allow the mixture to be reacted for polymerization at 140° C. for 4 hours and at 175° C. for 15 hours. Thereafter, the product was cooled down at room temperature and precipitated in ethanol to obtain a polymer resin.

The synthesized resin was solution-coated with a 10 wt % solution (solution DMSO). The resulting resin was dried at 100° C. in an oven for 24 hours. An ion-transfer separation membrane was immersed in a 1 M sulfuric acid ($H_2SO_4$) solution at 80° C. for 24 hours, and rinsed several times with distilled water (DI water), and then ionic conductivity was measured. The counter ion of sulfonic acid was substituted with $H^+$ instead of K.

Comparative Example 1

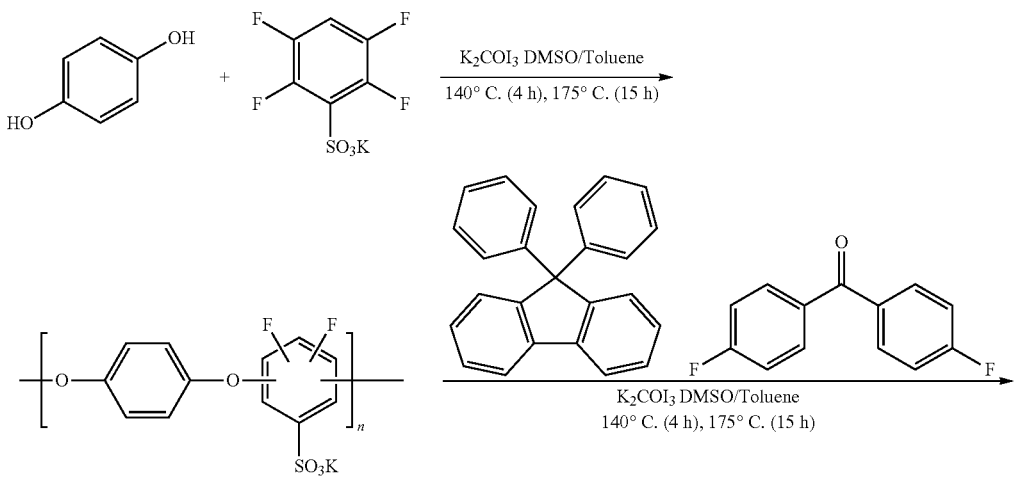

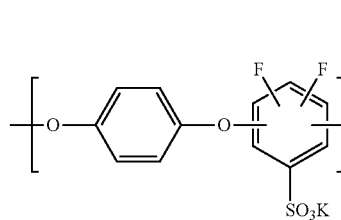
-continued
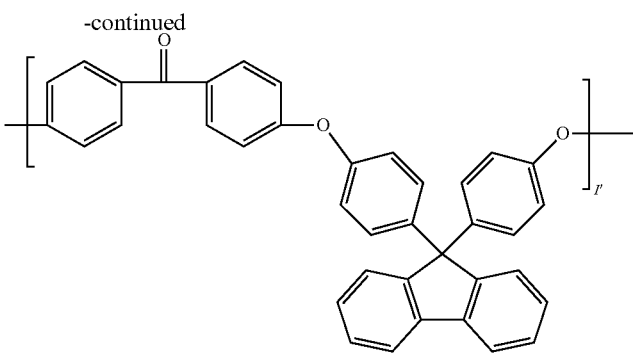

1,4-biphenol (0.001 mol) and a sulfonate-based tetra fluorine monomer (0.001 mol) were polymerized at 140° C. for 4 hours and at 175° C. for 15 hours, and polymerized by using dimethyl sulfoxide (DMSO) as a solvent, and thereafter, the resulting polymer was sufficiently cooled at room temperature, then a secondary monomer (0.0001 mol) was introduced thereto, and toluene and dimethyl sulfoxide (DMSO) were added thereto to allow the mixture to be reacted for polymerization at 140° C. for 4 hours and at 175° C. for 15 hours. Thereafter, the product was cooled down at room temperature and precipitated in ethanol to obtain a polymer resin.

An ion exchange resin was polymerized by using a monomer in which a sulfonic acid group is attached to the main chain without including a new monomer. The polymerized resin was used to prepare an ion exchange membrane in the manner as described above.

For the prepared ion exchange membrane, the result that the H$^+$ ionic conductivity was measured is shown in Table 1. (25° C., 100% humid conditions)

TABLE 1

| | Example 1 | Comparative Example 1 | Nafion 21 |
|---|---|---|---|
| H$^+$ ionic conductivity | 0.12 | 0.08 | 0.10 |

As can be seen from Table 1, it can be confirmed that when the sulfonate-based compound according to an exemplary embodiment of the present specification is included in polymer electrolyte membrane as the above-described unit, the ionic conductivity of the polymer was high in the case where a substituent corresponding to SO$_3$R$_2$ is linked to the chain in the p parenthesis, compared to the case where the substituent corresponding to SO$_3$R$_2$ is directly bonded to the main chain of the polymer. This means that the phase separation between the SO$_3$R$_2$ groups was facilitated and ionic conductivity was high. Furthermore, from the above result, it can be confirmed that the sulfonate-based compound according to an exemplary embodiment of the present specification may exhibit excellent efficiency in being applied to a H$^+$ ion transfer separation membrane of a fuel cell.

The invention claimed is:

1. A sulfonate-based compound of the following Formula 1:

[Formula 1]

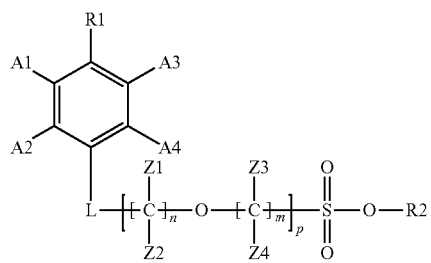

wherein:

A1 to A4 are the same as or different from each other, and are each independently a halogen group;

R1 is hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group;

L is a linking group including one or more of O, S, and SO$_2$;

Z1 to Z4 are each independently a halogen;

R2 is one of the elements of Group 1 of the periodic table;

n is an integer of 0 or more;

m is an integer of 0 or more;

p is an integer of 1 or more; and

{(n×p)+(m×p)} is an integer of 1 to 20, and wherein the sulfonate-based compound of Formula 1 is a compound of any one of the following Formulae 2-1 to 2-3:

[Formula 2-1]

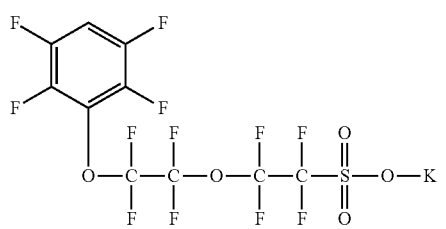

[Formula 2-2]

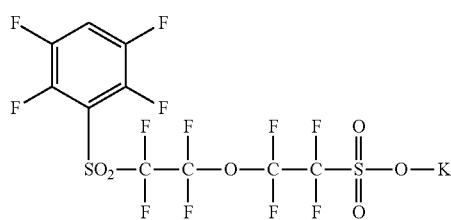

[Formula 2-3]

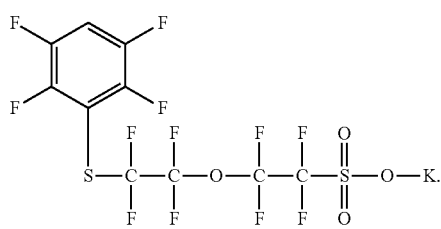

2. The sulfonate-based compound of claim 1, wherein Z1 to Z4 are each independently selected from the group consisting of F, Cl, Br.

3. A polymer electrolyte membrane comprising the sulfonate-based compound of claim 1.

4. The polymer electrolyte membrane of claim 3, wherein the polymer electrolyte membrane further comprises one or more polymers of a perfluorosulfonic acid polymer, a hydrocarbon-based polymer, polyimide, polyvinylidene fluoride, polyethersulfone, polyphenylene sulfide, polyphenylene oxide, polyphosphazine, polyethylene naphthalate, polyester, doped polybenzimidazole, polyether ketone, polysulfone, and acids or bases thereof.

5. A polymer electrolyte membrane comprising a polymer comprising a monomer derived from the sulfonate-based compound of claim 1.

6. The polymer electrolyte membrane of claim 5, wherein the polymer electrolyte membrane comprises a block-type copolymer comprising a hydrophilic block and a hydrophobic block.

7. The polymer electrolyte membrane of claim 6, wherein the hydrophilic block has a weight average molecular weight of 1,000 to 500,000 (g/mol) and the hydrophobic block has a weight average molecular weight of 1,000 to 500,000 (g/mol).

8. The polymer electrolyte membrane of claim 6, wherein the monomer derived from the sulfonate-based compound is included in a main chain of the hydrophilic block.

9. The polymer electrolyte membrane of claim 5, wherein ionic conductivity of the polymer electrolyte membrane is 0.03 s/cm to 0.2 s/cm.

10. The polymer electrolyte membrane of claim 5, wherein an ion exchange capacity value of the polymer electrolyte membrane is 0.5 to 3.

11. The polymer electrolyte membrane of claim 3, wherein the polymer electrolyte membrane comprises a polymer comprising a repeating unit of the following Formula 3 and a repeating unit of the following Formula 4:

[Formula 3]

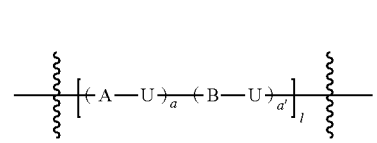

[Formula 4]

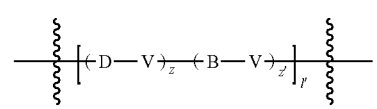

wherein in Formula 3;
 a is an integer more than 0;
 a' is an integer of 0 or more;
 a:a'=1,000:0 to 5:1; and
 l is an integer of 1 to 10,000; and
in Formula 4:
 Z is an integer more than 0;
 Z' is an integer of 0 or more;
 z:z'=1,000:0 to 5:1; and
 l' is an integer of 1 to 100,000; and
in Formulae 3 and 4:
 A, D, and V are the same as or different from each other, and are each independently one of the following Formulae 3-1 to 3-4:

[Formula 3-1]

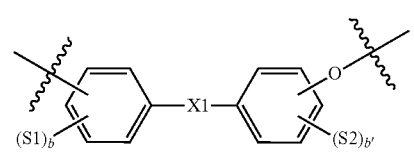

[Formula 3-2]

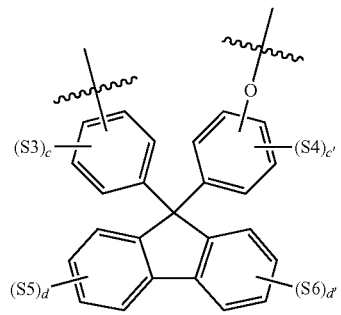

[Formula 3-3]

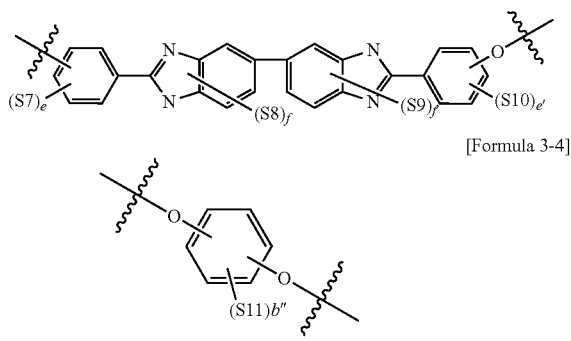

[Formula 3-4]

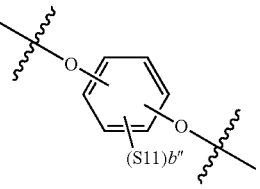

wherein in Formulae 3-1 to 3-4:
X1 is a direct bond, or one of —C(Z5)(Z6)-, —CO—, —O—, —S—, —SO$_2$—, and —Si(Z5)(Z6)-;
Z5 and Z6 are the same as or different from each other, and are each independently one of hydrogen, an alkyl group, a trifluoromethyl group (—CF$_3$), and a phenyl group;
S1 and S2 are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group;
b and b' are the same as or different from each other, and are each independently an integer of 0 to 4,
S3 to S6 are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group,
c, c', d and d' are the same as or different from each other, and are each independently an integer of 0 to 4;
S7 to S10 are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group;
e, e', f and f' are the same as or different from each other, and are each independently an integer of 0 to 4;
S11 is hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group; and
b" is an integer of 0 to 4;
and in Formula 3,
U is one of the following Formulae 4-1 to 4-4 and monomers derived from the sulfonate-based compounds:

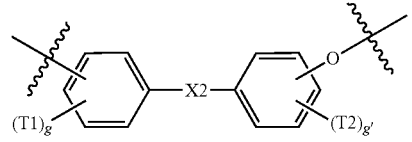

[Formula 4-1]

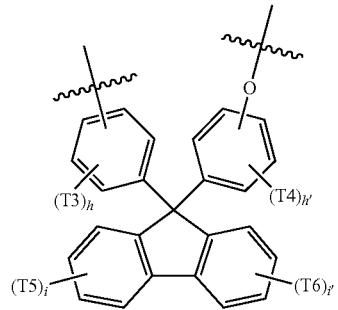

[Formula 4-2]

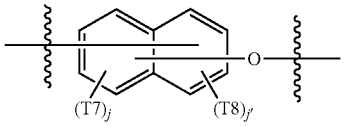

[Formula 4-3]

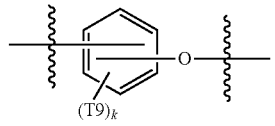

[Formula 4-4]

wherein in Formulae 4-1 to 4-4;
X2 is a direct bond, or —CO— or —SO$_2$—;
g and g' are the same as or different from each other, and are each independently an integer of 0 to 4;
h, h', i and i' are the same as or different from each other, and are each independently an integer of 0 to 4;
j and j' are the same as or different from each other, and are each independently an integer of 0 to 3;
each k is the same as or different from each other, and each independently is an integer of 0 to 4;
T1 to T9 are the same as or different from each other, at least one thereof are each independently —SO$_3$H, —SO$_3^-$M$^+$, —COOH, —COO$^-$M$^+$, —PO$_3$H$_2$, —PO$_3$H$^-$M$^+$, or —PO$_3^{2-}$ 2M$^+$, M is a metallic element, and the others are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group; and in Formulas 3 and 4, B is an entirely fluorine-based compound or partially fluorine-based compound, or is any one of the following Formulae 5-1 to 5-3;

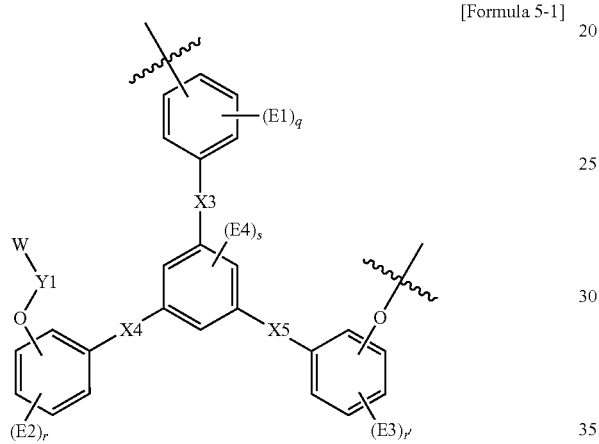

[Formula 5-1]

[Formula 5-2]

[Formula 5-3]

wherein in Formulae 5-1 to 5-3:

X3 to X5 are the same as or different from each other, and are each independently a direct bond, or —CO— or —SO$_2$—;

Y1 is a direct bond, or a $C_1$ to $C_{60}$ alkylene group;

E1 to E4 are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group;

q, r and r' are the same as or different from each other, and are each independently an integer of 0 to 4;

s is an integer of 0 to 3;

X6 is a direct bond, or —CO— or —SO$_2$—;

Y2 is a direct bond, or a $C_1$ to $C_{60}$ alkylene group;

E5 and E6 are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group;

t is an integer of 0 to 3;

t' is an integer of 0 to 4; and

X7 is a direct bond, or —CO— or —SO$_2$—,

Y3 is a direct bond, or a $C_1$ to $C_{60}$ alkylene group;

E7 and E8 are the same as or different from each other, and are each independently hydrogen, deuterium, a halogen group, a cyano group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group;

u is an integer of 0 to 3;

u' is an integer of 0 to 4; and

W is of the following Formula 6-1 in Formula 3, and of the following Formula 6-2 in Formula 4:

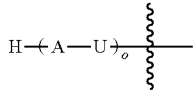

[Formula 6-1]

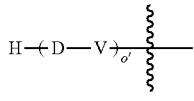

[Formula 6-2]

wherein in Formula 6-1, o is an integer of 1 to 10,000, and A and U are the same as that of A and U in Formula 1; and in Formula 6-2, o' is an integer of 1 to 100,000, and D and V are the same as that of D and V in Formula 2.

12. The polymer electrolyte membrane of claim 11, wherein A, D, and V are the same as or different from each other, and are at least one selected from the group consisting of:

and

R3 and R6 are the same as or different from each other, and are each independently a nitro group (—NO$_2$) or a trifluoromethyl group (—CF$_3$).

13. The polymer electrolyte membrane of claim 11, wherein U is at least one selected from the group consisting of:

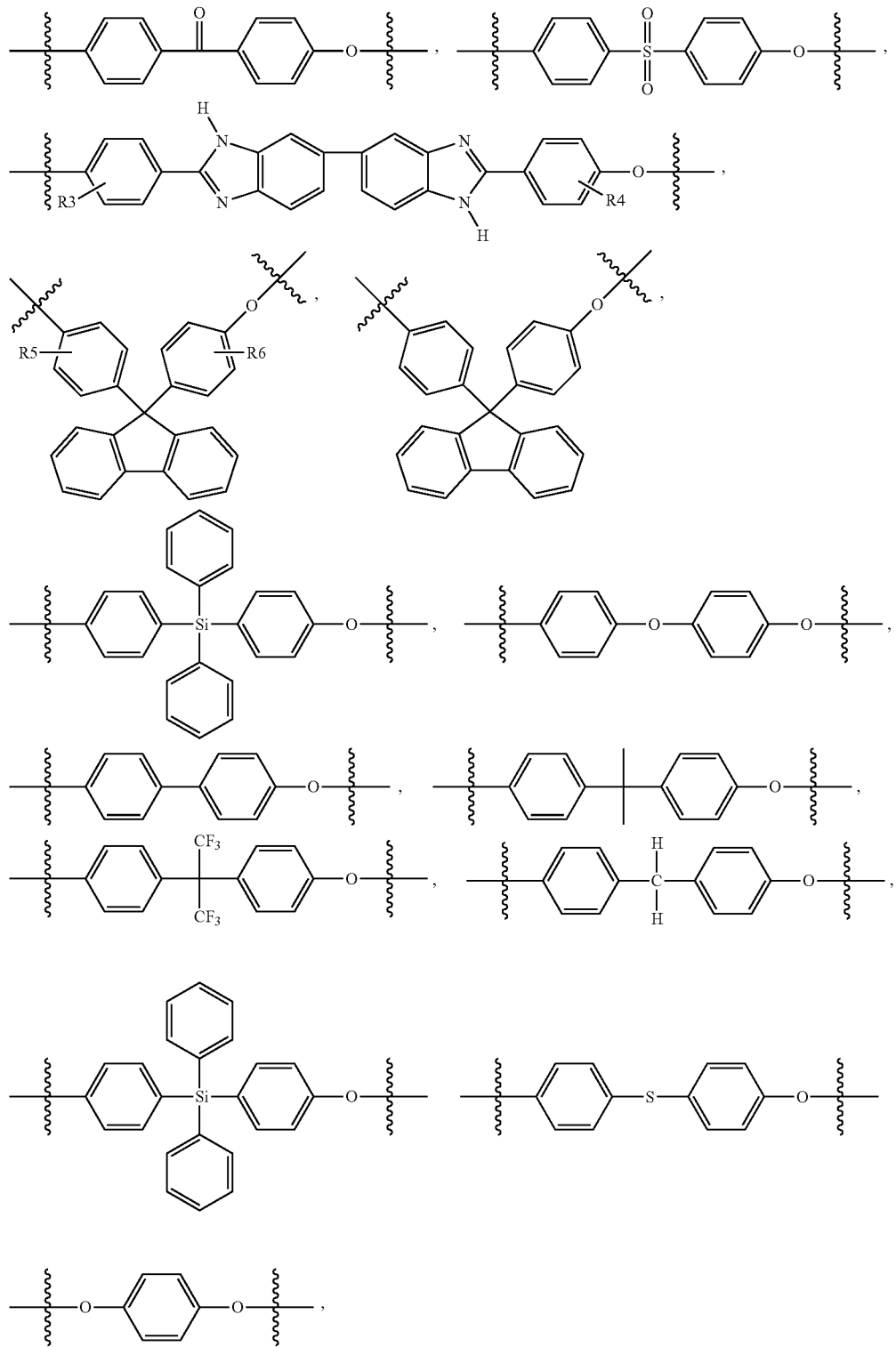

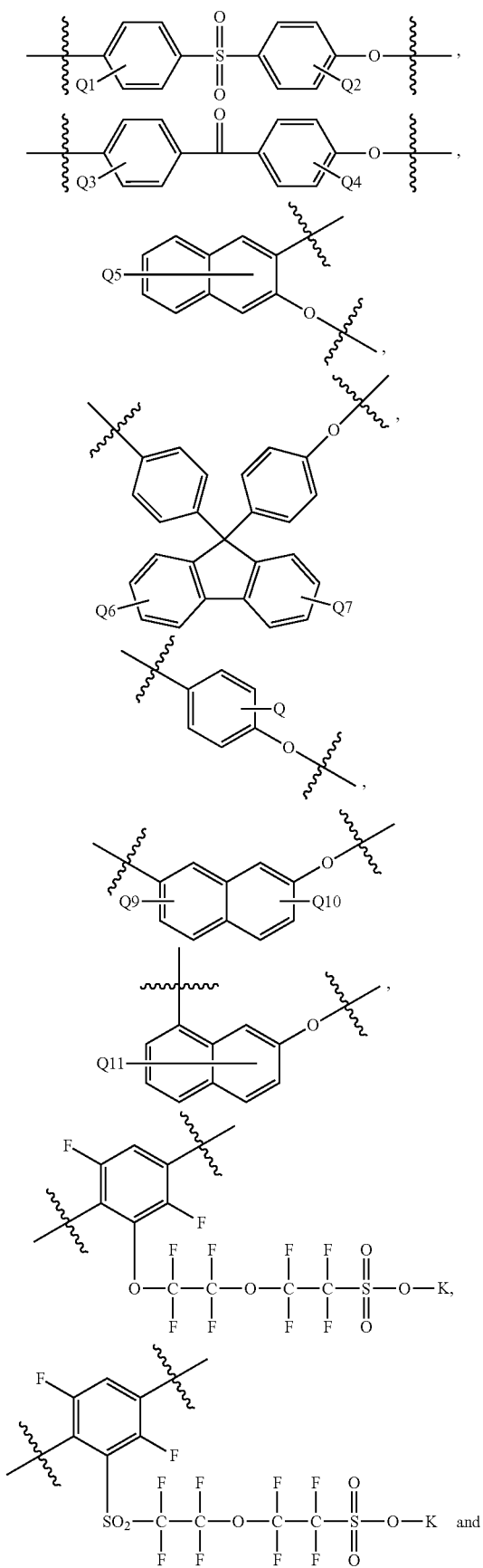
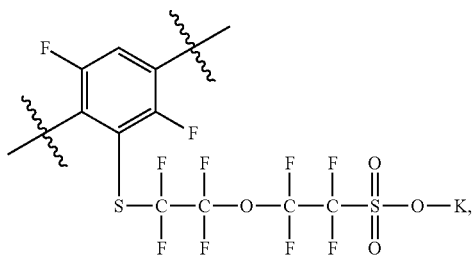
Q1 to Q11 are the same as or different from each other, and are each independently selected from the group consisting of hydrogen, —SO$_3$H, —SO$_3^-$M$^+$, —COOH, —COO$^-$M$^+$, —PO$_3$H$_2$, —PO$_3$H$^-$M$^+$, and —PO$_3^{2-}$2M$^+$; and
M is a metallic element.
14. The polymer electrolyte membrane of claim 11, wherein B is one selected from the group consisting of:
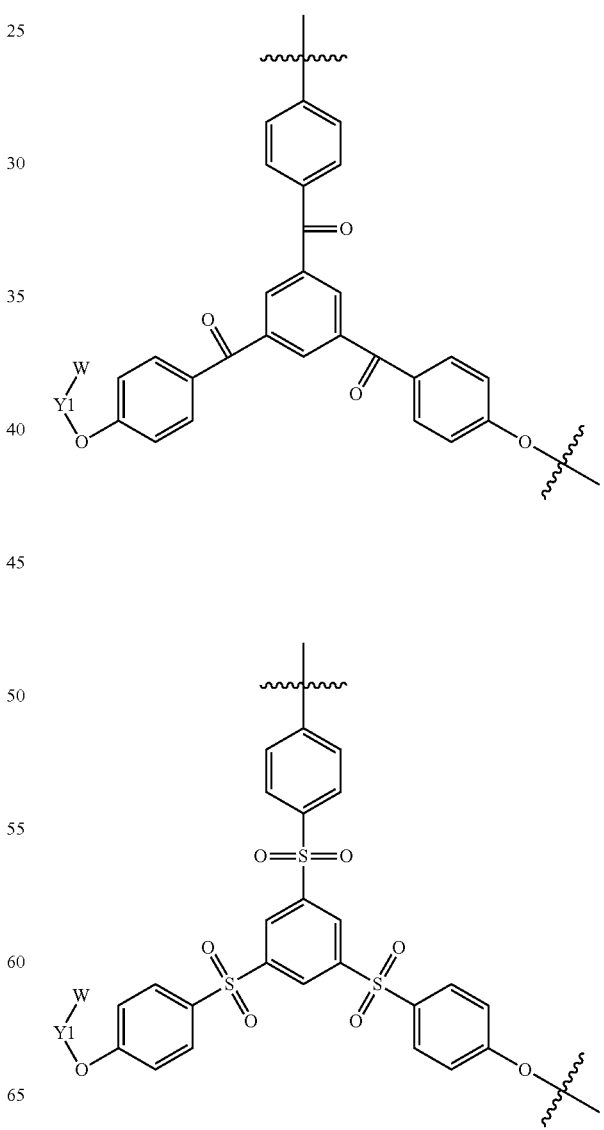

-continued

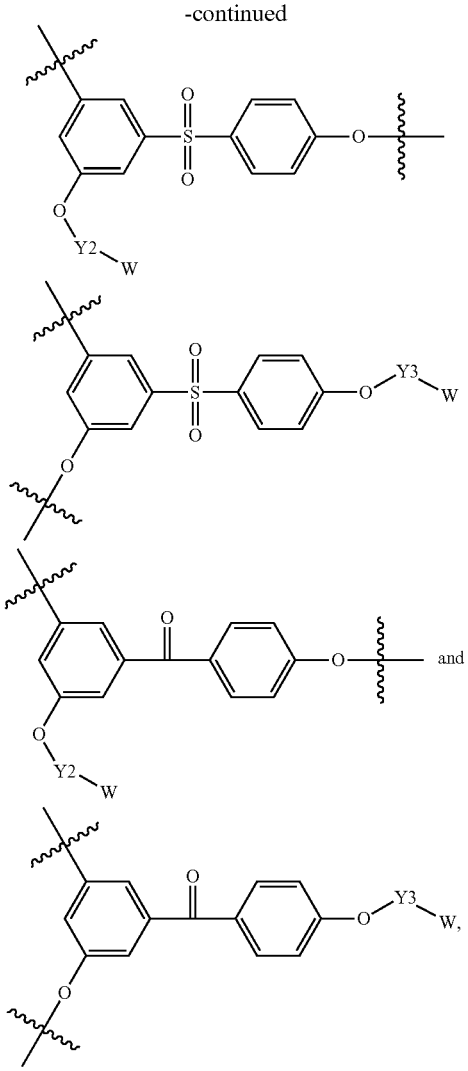

wherein:
Y1 to Y3 are the same as or different from each other, and are each independently a direct bond, or a C1 to C60 alkylene group;
W is a repeating unit of the following Formula 6-1 in Formula 3, and a repeating unit of the following Formula 6-2 in Formula 4:

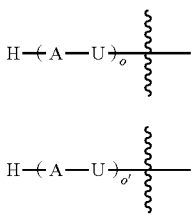

[Formula 6-1]

[Formula 6-2]

wherein:
in Formula 6-1, o is an integer of 1 to 10,000, and A and U are the same as that of A and U in Formula 3; and
in Formula 6-2, o' is an integer of 1 to 100,000, and D and V are the same as that of D and V in Formula 4.

15. A membrane-electrode assembly comprising:
an anode;
a cathode which is provided to face the anode; and
an electrolyte membrane which is provided between the anode and the cathode,
wherein the electrolyte membrane is the polymer electrolyte membrane of claim 3.

16. A polymer electrolyte-type fuel cell comprising:
a stack which includes the two or more membrane electrode assemblies of claim 15 and a bipolar plate interposed between the membrane electrode assemblies;
a fuel supply unit which supplies fuel to the stack; and
an oxidant supply unit which supplies an oxidant to the stack.

* * * * *